US011382348B2

(12) United States Patent
Giovannoni et al.

(10) Patent No.: US 11,382,348 B2
(45) Date of Patent: Jul. 12, 2022

(54) COMPOSITIONS FOR THE ADMINISTRATION OF APOA1 AND DOSAGES

(71) Applicant: GRG GENE TECHNOLOGY SA, Minusio (CH)

(72) Inventors: Roberto Giovannoni, Milan (IT); Gabriele Romano, Germignaga (IT); Nicola Fogher, Casalmaggiore CR (IT); Maria Rita Giuffre', Palermo (IT); Mariateresa Pettinato, Belvedere di Spinello (IT); Serena Reggi, Piacenza (IT)

(73) Assignee: GRG GENE TECHNOLOGY SA, Minusio (CH)

( * ) Notice: Subject to any disclaimer, the term of this patent is extended or adjusted under 35 U.S.C. 154(b) by 0 days.

(21) Appl. No.: 16/319,893

(22) PCT Filed: Jul. 31, 2017

(86) PCT No.: PCT/IB2017/054646
§ 371 (c)(1),
(2) Date: Jan. 23, 2019

(87) PCT Pub. No.: WO2018/025153
PCT Pub. Date: Feb. 8, 2018

(65) Prior Publication Data
US 2019/0246677 A1    Aug. 15, 2019

(30) Foreign Application Priority Data
Aug. 2, 2016  (IT) ............... 102016000081193

(51) Int. Cl.
*C07K 14/775* (2006.01)
*A23L 33/105* (2016.01)
*A61K 38/17* (2006.01)
*A23L 7/10* (2016.01)
*A61K 36/48* (2006.01)
*A23L 33/185* (2016.01)
*A61K 36/899* (2006.01)
*A23L 33/17* (2016.01)
*A61K 9/00* (2006.01)
*A61K 36/81* (2006.01)
*A61K 36/8998* (2006.01)

(52) U.S. Cl.
CPC .............. *A23L 33/105* (2016.08); *A23L 7/10* (2016.08); *A23L 33/17* (2016.08); *A23L 33/185* (2016.08); *A61K 9/0053* (2013.01); *A61K 36/48* (2013.01); *A61K 36/81* (2013.01); *A61K 36/899* (2013.01); *A61K 36/8998* (2013.01); *A61K 38/1709* (2013.01); *C07K 14/775* (2013.01); *A23V 2002/00* (2013.01); *A23V 2200/326* (2013.01); *A23V 2200/3262* (2013.01)

(58) Field of Classification Search
None
See application file for complete search history.

(56) References Cited

U.S. PATENT DOCUMENTS

| 6,258,596 B1 | 7/2001 | Benoit | |
|---|---|---|---|
| 2010/0212030 A1* | 8/2010 | Eyckerman | .......... C07K 14/775 800/4 |
| 2010/0222276 A1* | 9/2010 | Eyckerman | ............... A61P 9/10 514/4.8 |

FOREIGN PATENT DOCUMENTS

| WO | WO-2005047455 A2 | 5/2005 |
|---|---|---|
| WO | WO-2006012632 A2 | 2/2006 |
| WO | WO-2008017906 A1 | 2/2008 |
| WO | WO-2018025153 A1 | 2/2018 |

OTHER PUBLICATIONS

Hugh, et al, "Principles of Early Drug Discovery," British Journal of Pharmacology (2011) 162 1239-1249 (Year: 2011).*
Ansel, Allen, and Popovich, Pharmaceutical Dosage Forms and Drug Delivery Systems, 7th Edition, 1999, seven pages (Year: 1999).*
Giddings, G. et al., "Transgenic plants as factories for biopharmaceuticals," Nature Biotechnology 18(11):1151-1155, Nature Publishing Group, United Kingdom (2000).
International Search Report and Written Opinion for International Application No. PCT/IB2017/054646, dated Dec. 12, 2017, European Patent Office, Netherlands, 18 pages.
Mohamad, N., et al., "Human apolipoprotein Al mimetic peptides for the treatment of atherosclerosis," Current Opinion in Investigational Drugs 4(9):1100-1104, Pharmapress, United States (2003).
Nissen, S., et al., "Effect of Recombinant APOA-I Milano on Coronary Atherosclerosis in Patients with Acute Coronary Syndromes A Randomized Controlled Trial," Jama the Journal of American Medical Association 290(17):2292-2300, American Medical Association, United States (2003).
Stoffel, W. et al., "Transient Expression of Wild Type and Mutant Human Apolipoprotein Al in COS cells," Biological Chemistry, 372(7):481-488, Walter De Gruyter GMBH & CO, Germany, (1991).
Von Eckardstein, A., et al., "Structural analysis of human apolipoprotein A-I variants. Amino acid substitutions are nonrandomly distributed throughout the apolipoprotein A-I primary structure," J. Biol. Chem 265(15):8610-8617, American Society for Biochemistry and Molecular Biology, United States (1990).

* cited by examiner

*Primary Examiner* — Thomas S Heard
(74) *Attorney, Agent, or Firm* — Sterne, Kessler, Goldstein & Fox P.L.L.C.

(57) ABSTRACT

The present invention relates to new compositions for the oral administration of apolipoproteins in the dimeric or multimeric form, with specific dosage regimens for use in the treatment of atherosclerosis.

Figure 1:
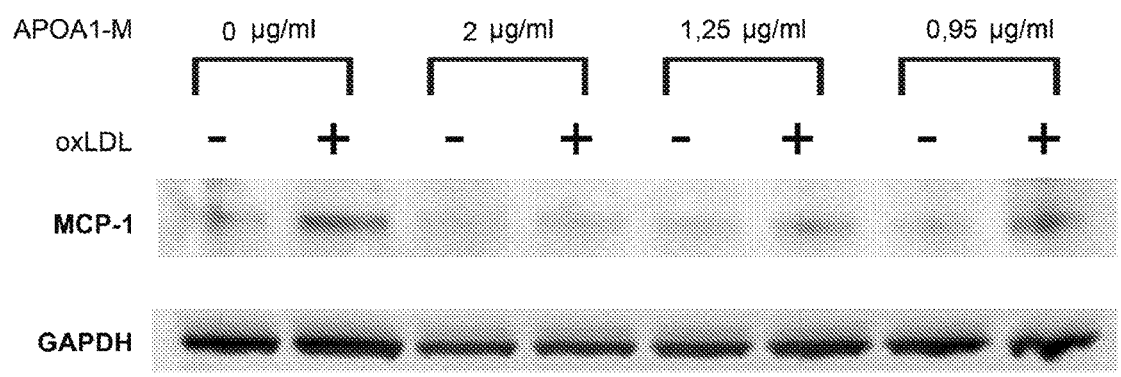
Figure 1:
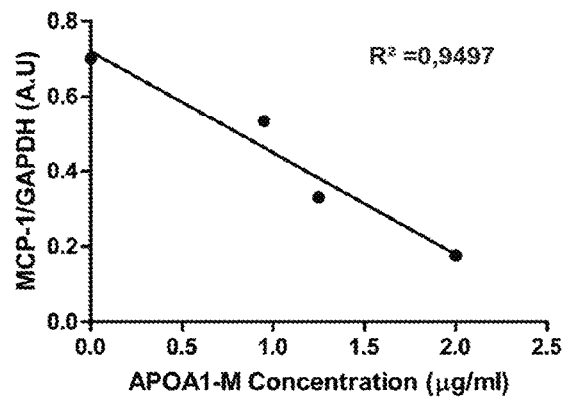

11 Claims, 7 Drawing Sheets
Specification includes a Sequence Listing.

A

B

COMPOSITIONS FOR THE ADMINISTRATION OF APOA1 AND DOSAGES

The present invention relates to new compositions for the oral administration of apolipoproteins in the dimeric or multimeric form, with specific dosage regimens for use in the treatment of atherosclerosis.

PRIOR ART

Myocardial infarction, stroke, unstable angina and sudden cardiac death collectively represent the main cause of death worldwide, with an ever-increasing incidence. The most common cause of these CVDs is atherosclerosis, a slowly progressing disease in which lesions, called plaques or atheromas, are formed in large- and medium-sized arteries. The atherogenic process is triggered by subendothelial retention of cholesterol-containing plasma lipoproteins in focal areas of arteries, particularly in anatomical districts (such as bifurcations, curvatures, etc.) where blood flow is characterized by turbulences.

High cholesterol levels in blood are associated with a disorder referred to as dyslipidemia, representing, both in a hereditary form and caused by secondary conditions not of genetic origin, a relevant risk factor for atherosclerosis. The increase of total cholesterol (TC) and LDL cholesterol (LDL-C, Low-Density Lipoprotein Cholesterol) in blood, as well as the so-called atherogenic lipid triad given by an increase of very low-density lipoproteins (VDLD), of small dense low-density lipoproteins and the reduction of HDL cholesterol (HDL-C, High-Density Lipoprotein Cholesterol), seem to be relevant factors for cardiovascular diseases. Early identification and management of modifiable risk factors, and above all of those factors contributing to dyslipidemias, constitute the first line of prevention for cardiovascular diseases.

The promising therapeutic potential of ApoA1 protein (Apolipoprotein A1) is known in the literature. The protein is found strongly associated with phospholipids, to form complexes and promote cholesterol outflow from cholesterol-rich cells. Maintaining an adequate plasmatic level of ApoA1, to mitigate or prevent atherosclerosis symptoms, is not easy to carry out.

The reverse correlation found between a high plasmatic level of HDL cholesterol and cardiovascular diseases is ascribed to the role that HDL and its major component, ApoA1 protein, have in the Reverse Cholesterol Transport—RCT phenomenon. RCT efficiency depends on ApoA1 protein ability to promote cholesterol outflow from cells, bind lipids, activate lecithin-cholesterol acyltransferase (LCAT) and form mature HDL which interacts with specific receptors and transfer proteins eliminating it from plasma flow through the liver.

It has been demonstrated that the infusion of proteins such as ApoA1 or ApoE, both recombinant and extraction ones, determine a reduction of the atherosclerotic burden in animal experimental models of atherosclerotic disease. Although various studies on animal models of atherosclerosis have demonstrated the potential of HDL use as a therapeutic strategy, clinical studies did not substantially succeed to demonstrate a significant reduction in atheroma volume, an important effectiveness parameter, when recombinant HDL molecules or the related HDL-mimetic peptides have been administered by infusion [A. M. Fogelman, Trying to harness the potential of HDL: wishful thinking or sound strategy? Eur Heart J. 35 (2014) 3248-3249.]. The therapies targeting HDL cholesterol for atherosclerosis are based on normalization of HDL-C plasma levels by acting on different sides of reverse cholesterol transport metabolism. Among these, statins are used to reduce endogenous cholesterol synthesis in the liver, thereby reducing LDL-C levels. On the other hand, CETP inhibitors increase HDL-C levels. Other therapeutic approaches are based on the infusion of reconstituted HDL and ApoA1 mimetics in the bloodstream. With this type of molecules, the aim is to increase the amount of cholesterol in HDL particles, and thereby improve the functionality of these molecules. These strategies yielded relevant results in experimental models, which however did not lead to a clear advantage in clinical studies.

Regardless of the actual clinical application, and despite the high therapeutic potential of ApoA1 lipoproteins, their therapeutic use in disorders associated with dysfunctions or anomalies of lipid metabolism (such as familial hypercholesterolemia, atherosclerosis, and others) has not been satisfactorily exploited yet. There are two main limitations accounting for the lack of success of ApoA1-based therapies, i.e. the very low efficiency of methods for the production and/or purification of these molecules, and the limits in their administration to patients in need thereof.

An integral part of therapies currently in use for the treatment of atherosclerosis is the substantial modification of the patient's dietary habits. Such a modification, since often required for persons hardly able to control their dietary habits, is oft-times a failure and seriously undermines the effectiveness and results of pharmacological therapies used on patients. The relevance of diet in the treatment of the above-indicated pathologies is well-known in the literature (e.g. Connor W E, Connor S L "Importance of diet in the treatment of familial hypercholesterolemia" Am J Cardiol. 1993 Sep. 30; 72(10):42D-53D; Connor W E, Connor S L "Diet, atherosclerosis, and fish oil" Adv Intern Med. 1990; 35:139-71; Chapman M J, Blankenberg S, Landmesser U (2016) The year in cardiology 2015: prevention. Eur Heart J 37:ehv721-519. doi: 10.1093/eurheartj/ehv721).

Patent Application WO2008/01790 describes the production in plant seeds of muteins of ApoA1 in the dimeric or multimeric form and assumes, without however demonstrating it, not only an intravenous administration of these apolipoproteins, but also an oral or a rectal one. In the oral administration, an administration is assumed directly by administering milk extracted from seeds of plants described in the patent application, or from flours thereof, etc.

Moreover, the document teaches a daily dosage of Apolipoproteins A1 by pharmaceutic compositions comprising one or more dimers and/or oligomers of the muteins described in pharmaceutically effective concentrations, such as, e.g., 10 mg/Kg of body weight, or 50 mg/Kg of body weight.

SUMMARY OF THE INVENTION

The Authors of the present invention have verified the possibility of effectively using an oral administration, by milk extracted from seeds of plants as described in WO2008/017906, and by assessing the activity thereof in various cell and animal models.

However, the Authors of the present invention have surprisingly discovered that the administration of milk extracted from seeds of plants as described in WO2008/017906 was effective, in vivo, at dosages 10-100-fold lower than those suggested in the above-indicated Patent Application, and that the anti-atherosclerotic therapeutic effect was observable also in animals subjected, during treatment with the assayed oral composition, to a hypercholesterolizing diet.

The Authors have also advantageously discovered that milk extracted from the seeds of plants as described in WO2008/017906 retained its effectiveness also in lyophilized form, after storage of the frozen lyophilizate (e.g., −20° C.), or at room temperature and after resuspension thereof with an appropriate diluent.

In in vivo experiments on mice treated with a hypercholesterolemic diet, said composition proved surprisingly capable of preventing the progression of atherosclerotic plaques, but also of significantly reducing their area, also in animals subjected, before and after treatment, to a hypercholesterolizing diet.

In the literature, there are no experimental data on oral administration of apolipoprotein A1 (ApoA1) or muteins thereof, data that would therefore enable to assume correct dosage regimens; on top of that, existing data on intravenous administration of said molecules (see Ibanez et al, Atherosclerosis 2012, and Cimmino et al, J Cell Mol Med 2009, reporting the administration of 75 mg/Kg of APOA1Milano to hypercholesterolemic and atherosclerotic rabbits, in two IV infusions 4 days apart, for a total of 150 mg/Kg in a week) show, at dosages much higher than those described and claimed herein for oral administration, a <5% reduction of the atherosclerotic plaque.

In data reported in the present description, a plaque reduction of about 50% at the level of the aortic sinus, and a plate area reduction 40% in the aortic arch are demonstrated.

Such data were moreover obtained on mice fed with a hypercholesterolemic diet, reflecting much more realistically a possible dietary regimen of patients not especially disciplined at the dietary level.

Therefore, object of the invention is a composition comprising one or more muteins of apolipoprotein A1 (ApoA-1) in the dimeric and/or multimeric form, wherein said muteins are produced in the dimeric and/or multimeric form in plant seeds, said composition comprising milk extracted from seeds of said plants and/or derivatives thereof, and wherein said muteins are administered orally to patients in a daily dosage of from 0.2 to 4 mg/kg of body weight for use in the treatment of atherosclerosis.

Object of the invention is also a method for the treatment of atherosclerosis by oral administration, to a patient in need thereof, of a composition comprising one or more muteins of apolipoprotein A1 (ApoA1) in the dimeric and/or multimeric form, wherein said muteins are produced in the dimeric and/or multimeric form in plant seeds, said composition comprising milk extracted from seeds of said plants and/or derivatives thereof, and wherein said muteins are administered in a daily dosage of from 0.2 to 4 mg/kg of body weight.

DETAILED DESCRIPTION OF THE FIGURES

FIG. 1. ApoA-1M in rice milk is more effective than recombinant ApoA-1 in preventing macrophage activation.

A. Representative immunoblot for MCP-1 on lysates of THP-1 macrophages (ATCC® TIB-202™). The figure is representative of 5 independent experiments. THP-1 macrophages were incubated with rice milk containing ApoA1-M (according to what described in Patent Application WO2008/017906) at a concentration equal to 2 µg/ml, or, as control, with ApoA1-R at a concentration of 2 µg/ml. B. MCP-1 expression was significantly induced by oxLDL administration. Only milk-contained ApoA1-M, and not ApoA1-R, was able to inhibit MCP-1 expression in THP-1 macrophages. *p<0.05. Error bars represent the standard error of the mean (SEM).

Figure 2:
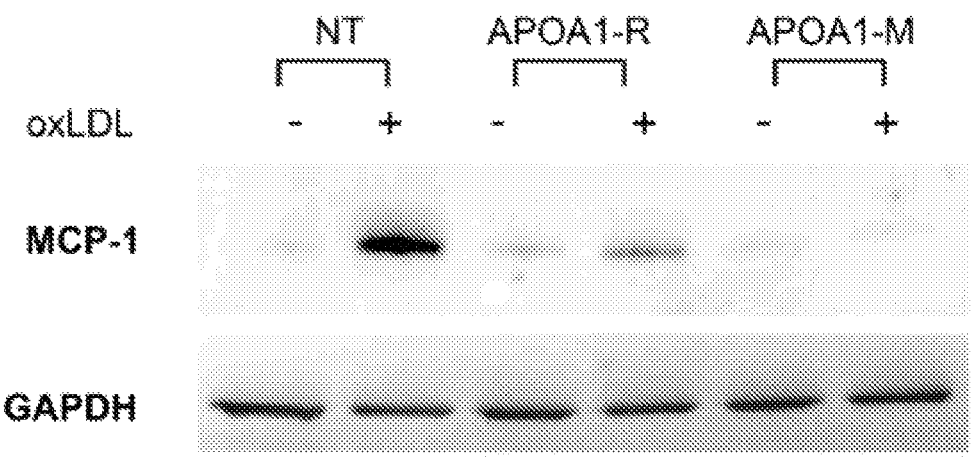
Figure 2:
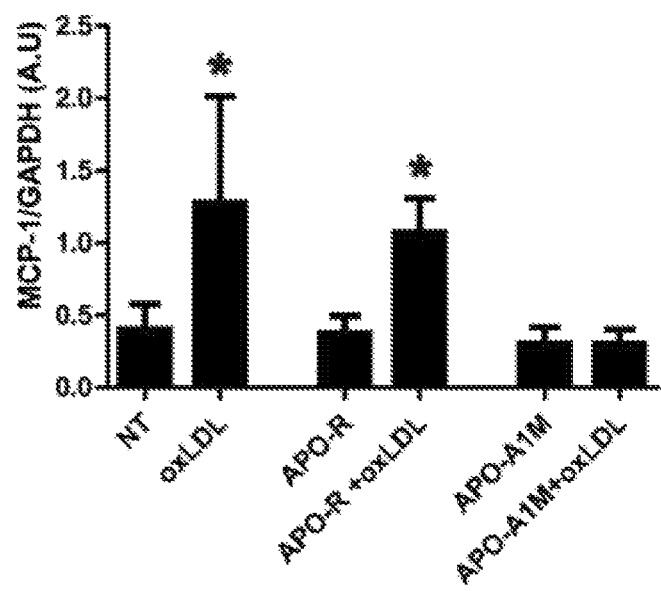

FIG. 2. ApoA-1Milano (ApoA1-M) mutein in rice milk reduces oxLDL-induced MCP-1 expression by THP-1 macrophages.

A. Representative immunoblot for MCP-1 on lysates of THP-1 macrophages. The figure is representative of 5 independent experiments. ApoA-1Milano concentration in rice milk is indicated in panel A. B. MCP-1 expression was inversely proportional to ApoA1-M concentration in rice milk.

Figure 3:
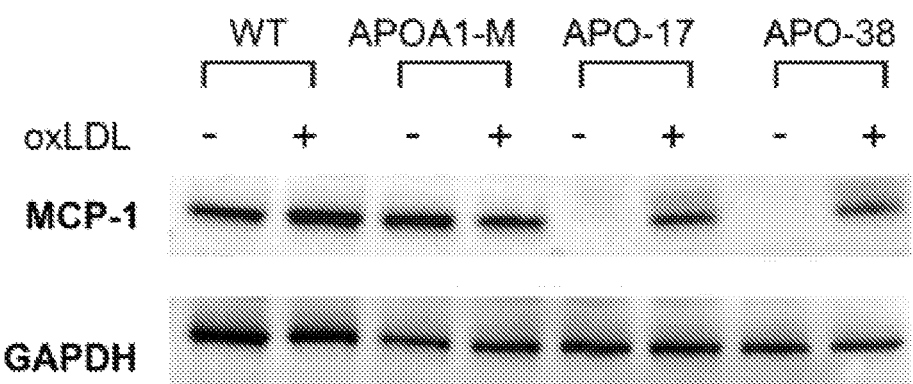
Figure 3:
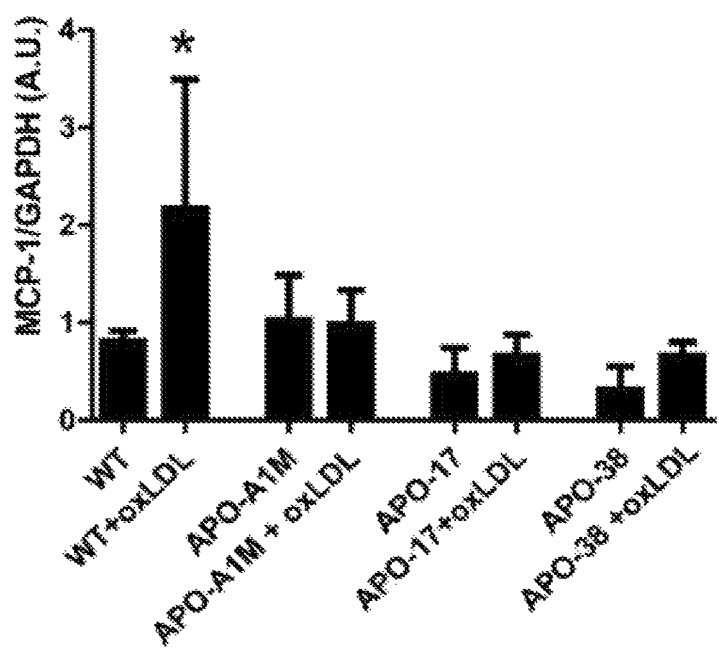

FIG. 3. ApoA-1 173-215 (APO-17) and ApoA-1 151-173 (APO-38) muteins, present in milk derived from the corresponding rice plant clones (described in Patent Application WO2008/017906), were effective in preventing THP-1 activation at lower concentrations of ApoA-1Milano (APOA1-M) in rice milk (always prepared according to Patent Application WO2008/017906).

A. Representative immunoblot for MCP-1 on lysates of THP-1 macrophages. The figure is representative of 5 independent experiments. The concentration of ApoA-1Milano, administered by rice milk, was equivalent to 2 µg/ml, whereas that of ApoA-1 173-215 (APO-17) and ApoA-1151-173 (APO-38) muteins, administered by rice milk, was of 1.5 µg/ml and 1.6 µg/ml, respectively. B. MCP-1 expression was significantly induced by oxLDL administration. Equivalent concentration of WT rice milk did not influence MCP-1 production, unlike rice milk containing the ApoA-1Milano (ApoA1-M), ApoA-1 173-215 (SEQ ID 8, APO-17) and ApoA-1 151-173 (SEQ ID 34, APO-38) muteins. Double mutant clones ApoA-1 173-215 (SEQ ID 8, APO-17) and ApoA-1 151-173 (SEQ ID 34, APO-38) were effective at lower concentrations compared to ApoA1-M in rice milk. *p<0.05. Error bars represent SEM.

Figure 4:
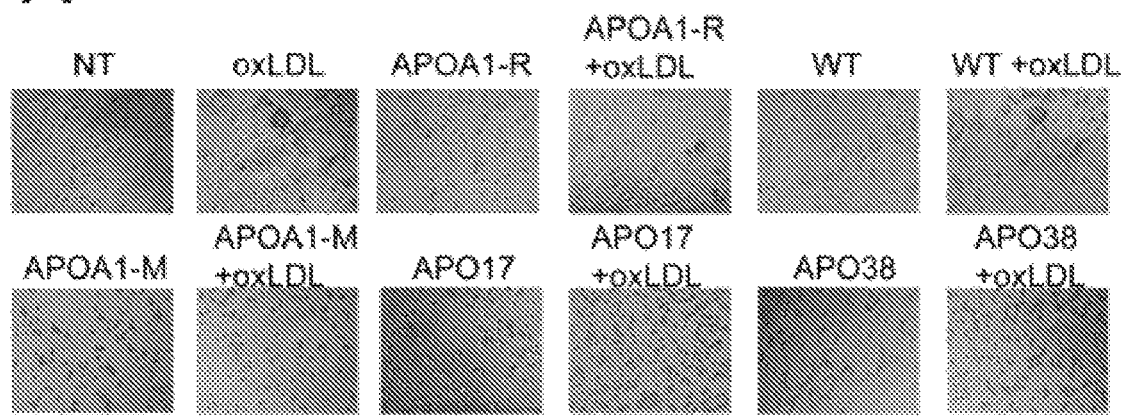
Figure 4:
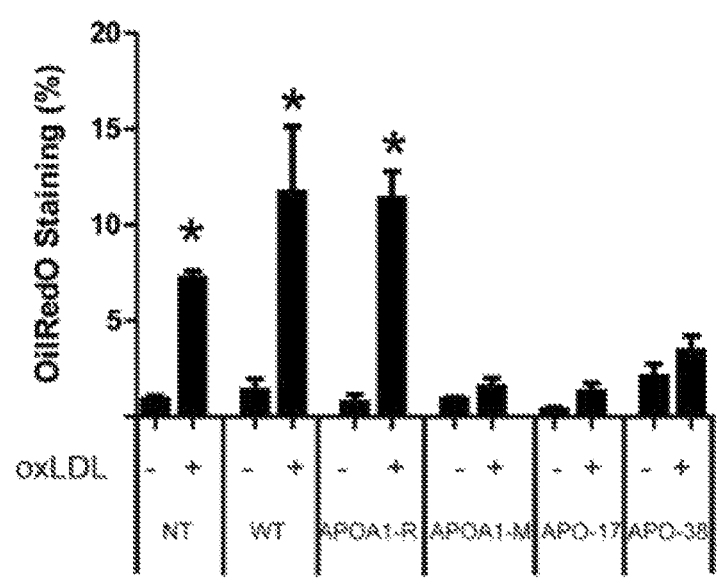

FIG. 4. ApoA-1 muteins-containing rice milk inhibited lipid accumulation in THP-1 macrophages.

A. figure representative of Oil Red O staining of 3 independent experiments. The concentration of ApoA-1Milano, carried to macrophages by rice milk, was of 2 µg/ml, whereas that of ApoA-1 173-215 (APO-17) and ApoA-1 151-173 (APO-38) muteins was of 1.5 µg/ml and 1.6 µg/ml, respectively. B. Oil Red O staining was significantly reduced by the administration of rice milk containing ApoA-1Milano (APOA1-M), ApoA-1 173-215 (APO-17) and ApoA-1 151-173 (APO-38) muteins *p<0.05. Error bars represent SEM.

Figure 5:
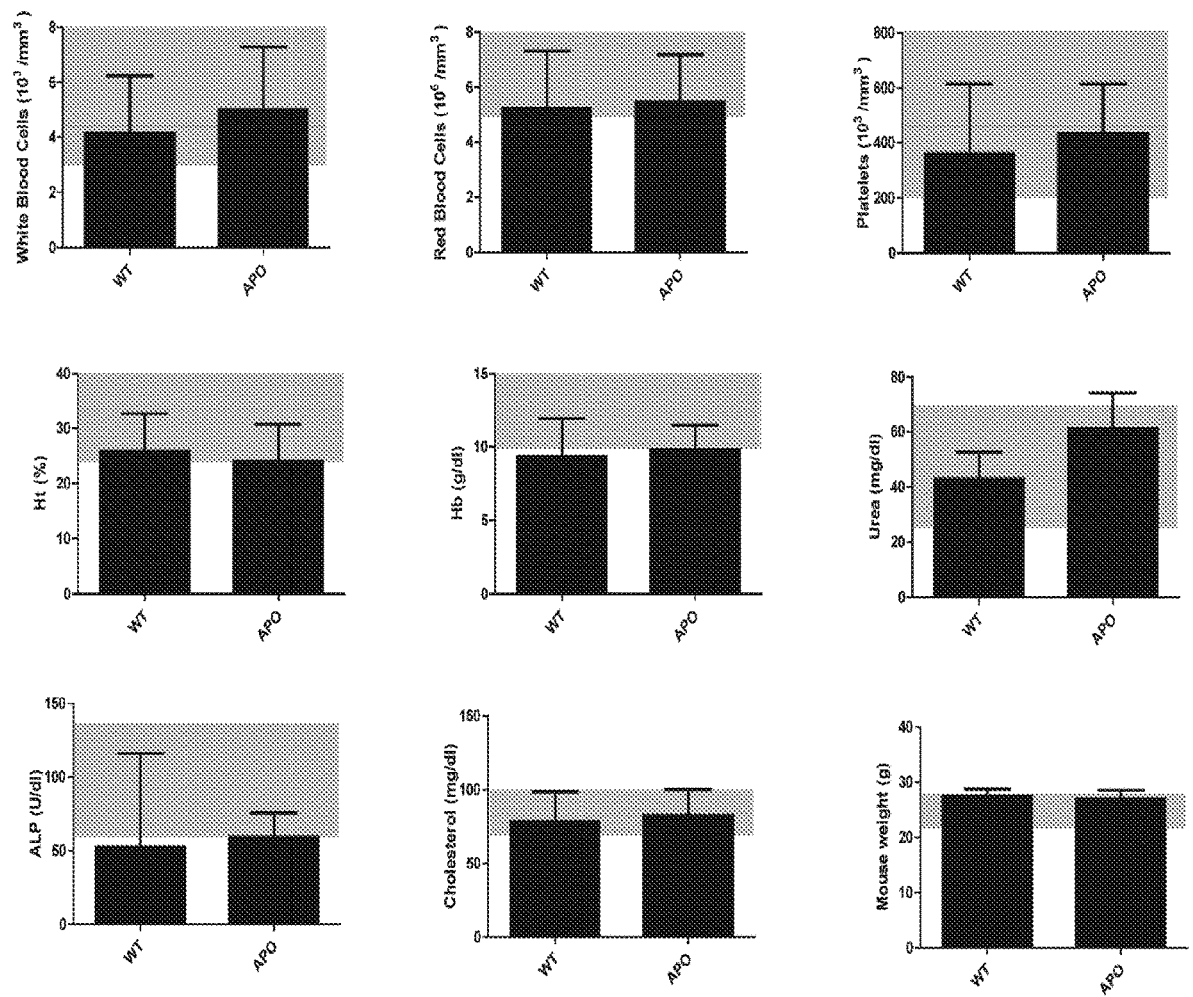

FIG. 5. wild-type (WT), or ApoA-1M (APO)-containing rice milk is well-tolerated by C57BL/6J strain mice.

WT or ApoA-1Milano mutein-containing rice milk was administered to 8-10-week-old male mice for 15 days, 5 g/week. Hematological and biochemical-clinical analyses showed no sign of suffering. Kidney and liver functions were not found altered. Ht=hematocrit; Hb=hemoglobin; ALP=alkaline phosphatase. Grey areas represent the range of normal values for wild-type (WT) animals of murine strain C57BL/6J based on datasets of the Mouse Phenome Database project (http://phenome.jax.org/). Error bars represent SEM.

Figure 6:
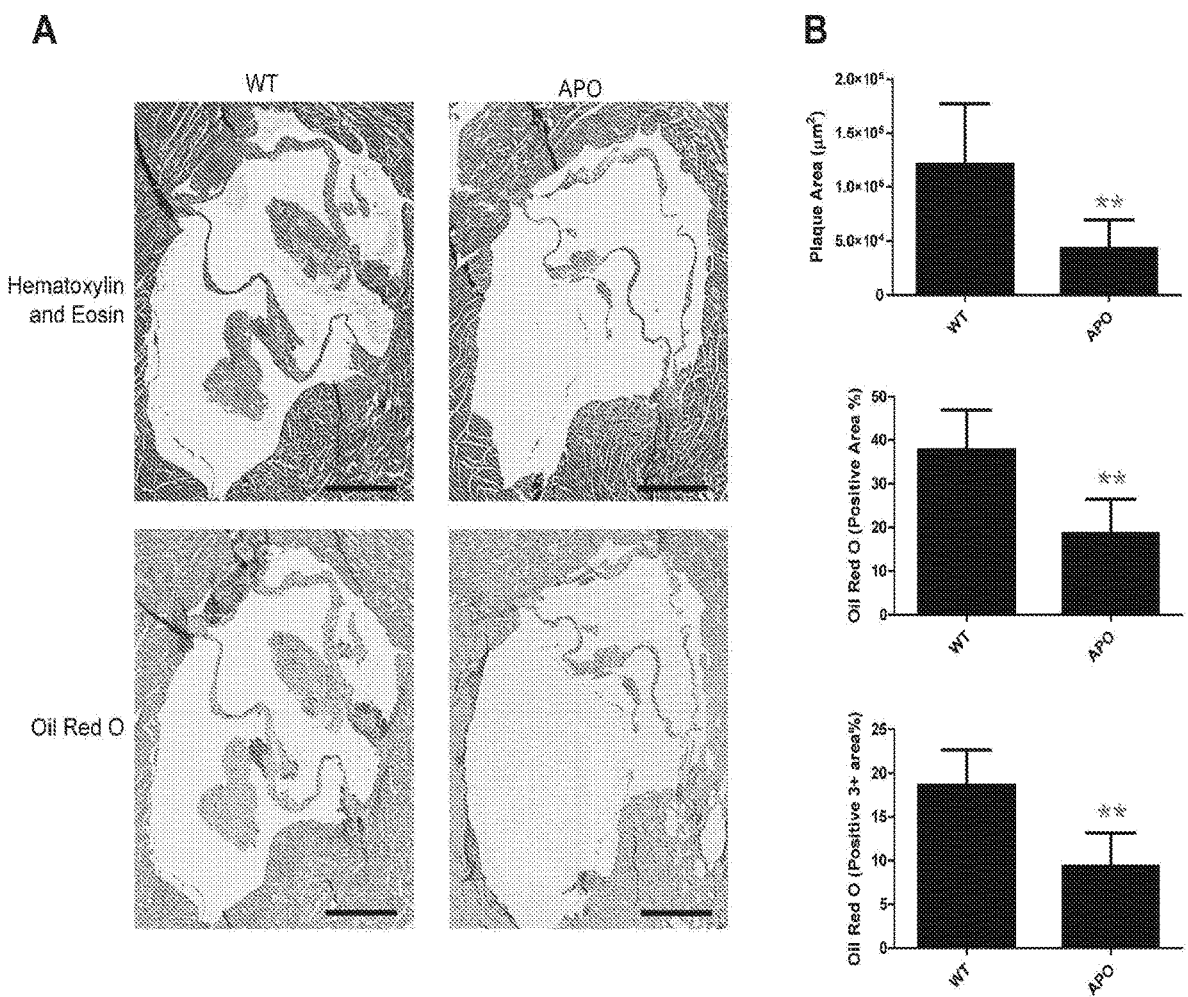

FIG. 6. ApoA-1 Milano (APO)-containing milk is able to reduce plaque extension in B6.129P2-Apoe$^{tm1Unc}$/J mice subjected to high-fat diet.

A. Figure representative of hematoxylin/eosin (top panels) and Oil Red O (bottom panels) staining of sections of aortic sinuses from homozygous B6.129P2-Apoe$^{tm1Unc}$/J mice fed with a high-fat diet, treated with WT rice milk or rice milk containing ApoA-1Milano (APO) dimer for 15 days, 5 g/week (respectively depicted in left-side and right-side panels). Bars represent 500 µm. B. Rice milk containing ApoA-1Milano (APO) dimers significantly reduced plaque area (top panel) and the area positive to Oil Red O staining (center panel). Rice milk containing ApoA-1Milano (APO) dimers decreased also Oil Red O staining intensity (bottom panel); **p<0.01. Error bars represent SEM.

Figure 7:
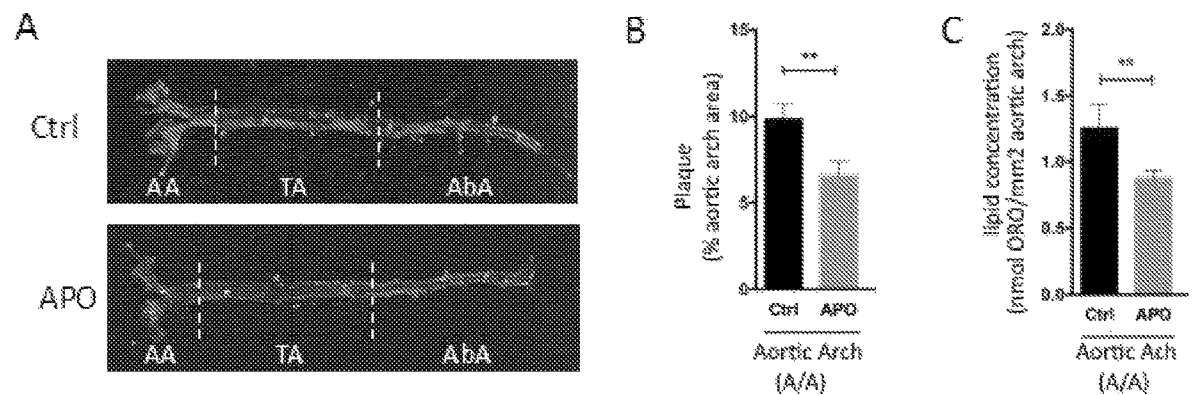

FIG. 7. ApoA-1Milano (APO)-containing rice milk reduces atherosclerotic plaques and their lipid content in the aortic arch of B6.129P2-Apoe$^{tm1Unc}$/J mice fed a high-fat diet.

A. Representative images of aortas, processed according to the 'en face' technique and incubated with Oil Red O, of homozygous B6.129P2-Apoe$^{tm1Unc}$/J mice fed a high-fat diet, treated with WT rice milk (Ctrl, n=6) or rice milk containing ApoA-1Milano (APO, n=8) for 15 days, 5 g/week. Oil Red O staining is indicated in red. AA: Aortic Arch; TA: Thoracic Aorta; AbA: Abdominal Aorta. B. ApoA-1Milano (APO)-containing rice milk significantly reduced atherosclerotic plaque area in the Aortic Arch, the section of the aorta in which the onset of atherosclerotic plaque is most frequent. Lipid lesions at the level of Aortic Arch (AA) are expressed as percent of Aortic Arch area using ImageJ software. C. ApoA-1Milano (APO)-containing rice milk significantly reduced lipid concentration in the Aortic Arch, the section of the aorta in which the onset of atherosclerotic plaque is most frequent. Lipid lesions are expressed as concentration of solubilized Oil Red O per square millimeter of Aortic Arch (AA) area. Error bars represent the mean±the standard error of the mean; ** p<0.01 (B, C).

Figure 8:
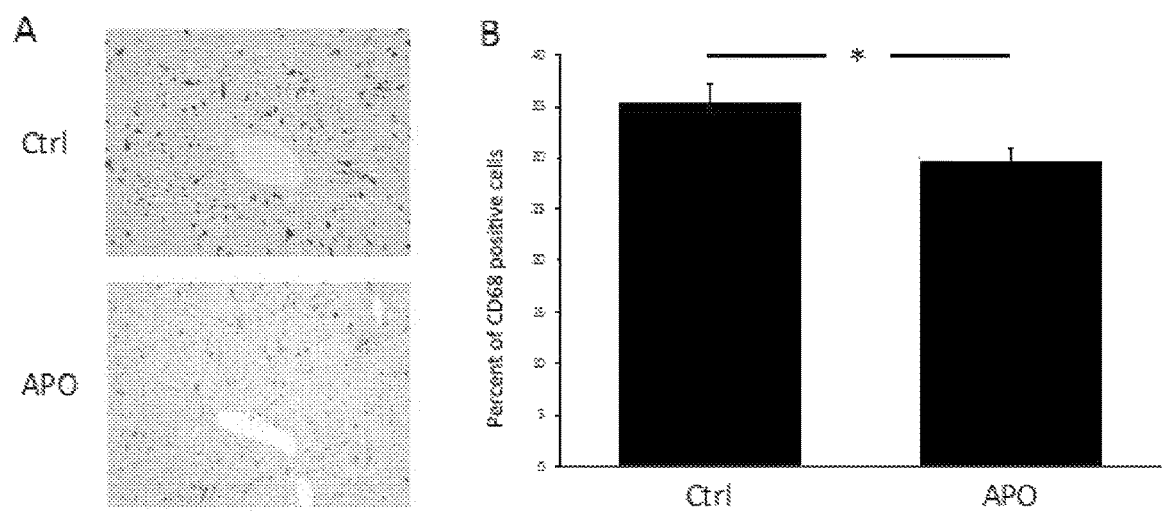

FIG. 8. ApoA-1Milano (APO)-containing rice milk reduces the number of macrophages in the liver of B6.129P2-Apoe$^{tm1Unc}$/J mice fed a high-fat diet.

A. Representative images of liver sections labeled for CD68 antigen in immunohistochemistry experiments, of homozygous B6.129P2-Apoe$^{tm1Unc}$/J mice fed a high-fat diet, treated with WT rice milk (Ctrl, n=5) or ApoA-1Milano-containing rice milk (APO, n=7) for 15 days, 5 g/week. B. ApoA-1Milano (APO)-containing rice milk significantly reduced the percent of CD68 marker-positive macrophages, in livers of homozygous B6.129P2-Apoetm1Unc/J mice fed a high-fat diet. Error bars represent the mean±the standard error of the mean; *p<0.05

In all experiments, the rice milk containing ApoA-1 dimers was comprised of milk of rice seeds derived from plants produced as described in WO2008/017906, in which the ApoA-1 muteins are directly expressed in the dimeric and/or multimeric form (depending on the number of cys mutations that were inserted therein) in seed tissues.

In the text, by "Apo" it is always meant ApoA-1, whose wild-type form is that reported in sequence 40.

DETAILED DESCRIPTION OF THE INVENTION

As mentioned above, therefore, object of the invention is a composition comprising one or more muteins of apolipoprotein A1 (ApoA-1) in the dimeric and/or multimeric form, wherein said muteins are produced in the dimeric and/or multimeric form in plant seeds, said composition comprising milk extracted from seeds of said plants and/or derivatives thereof, and wherein said muteins are administered orally to patients in a daily dosage of from 0.2 to 4 mg/kg of body weight for use in the treatment of atherosclerosis.

The in-seed production method of the dimeric/multimeric form of human ApoA-1 muteins is described in detail in Patent Application WO2008/017906.

The muteins and the seeds used in the present application are produced exactly as described in Patent Application WO2008/017906.

In short, also according to the present invention, uses expression cassettes capable of directing in plant seeds the synthesis of heterologous apolipoproteins, wherein said apolipoproteins, by virtue of sequences mutagenized in a controlled way and for the purpose, are mainly accumulated as dimers and/or oligomers.

An expression cassette useful for the carrying out of modified plants capable of producing the seed milk as indicated above comprises a promoter of a plant gene specific for the expression in storage organs of the seed. A non-limiting example of such promoters is represented by: the prolamine promoter of rice, pPROL (Accession number AF156714), described in PCT/IT B2003/05092, or the glutelin promoter of rice pGluB-1 (Accession number AY427569) or pGluB-4 (Accession number AY427571) described in Quing and Takawa 2004, Plant Biotech. J. 2:113-115, for expression in cereals, or the soybean 7S basic globulin, or the beta-conglycinin promoter of soybean described in WO00/04146, for the expression in plants belonging to the leguminous and Solanaceae plants. The promoters of glutelins, mentioned above, are particularly advantageous for the expression in all those seeds such as rice, barley, spelt, etc., that undergo industrial dehusking, because they direct the expression in a diffuse manner throughout all the endosperm of the seed. The expression cassette will further comprise a DNA sequence coding for a signal sequence of a plant protein capable of directing the Apo mutein to the storage organs of the seed so as to obtain the accumulation of said protein in the dimeric or multimeric form, depending on the number of cysteines present in the considered mutein. Non-limiting examples of a suitable signal sequence are represented by the signal sequence of the rice prolamine gene (Accession number AF156714) or of the glutelin genes from rice (Accession n. AY427569 and AY427571), or of the globulin and beta-conglycinin genes of soybean (patent WO00/04146). The cassette will also comprise a DNA sequence coding for a mutein of human apolipoprotein, capable of forming dimers and/or oligomers comprising three or more monomers.

Starting from the sequence coding for human ApoA-1 (SEQ ID 40, reported below), non-limiting examples of mutations suitable for the muteins of the invention are: SEQ ID 2 Mutation R173C; SEQ ID 4 Mutation R123C; SEQ ID 6 Mutation R215C; SEQ ID 8 Mutation R173C-R215C; SEQ ID 10 Mutation R123C-R215C; SEQ ID 12 Mutation R100; SEQ ID 14 Mutation R61C; SEQ ID 16 Mutation R83C, SEQ ID 18 Mutation R151C; SEQ ID 20 Mutation R10C-R215C; SEQ ID 22 Mutation R61C-R173C; SEQ ID 24 Mutation R61C-R215C; SEQ ID 26 Mutation R61C-R151C; SEQ ID 28 Mutation R83C-R173C; SEQ ID 30 Mutation R83C-R151C; SEQ ID 32 Mutation R83C-R215C; SEQ ID 34 Mutation R151C-R173C; SEQ ID 36 Mutation R151C-R215C; SEQ ID 38 Mutation R10C-R173C. The nucleotide sequences coding for the above-described muteins are immediately deducible from the said amino acid sequences. Given the correspondence of each codon with a specific amino acid, it is sufficient to have the amino acid sequence to go back to any nucleotide sequence coding it. The nucleotide sequences coding for the above-mentioned muteins are therefore considered described by the description of the amino acid sequence coded by them. It is unquestionable that an amino acid sequence per se gives the necessary information for the knowledge of any nucleotide sequence coding it.

Said muteins can be obtained by all standard techniques known to a person skilled in the art; for instance, it is possible to carry out the replacement of amino acids in defined positions by site-directed mutagenesis. Examples of muteins suitable for the carrying out of the invention are those reported above, however the invention is not limited to them but comprises also other muteins of the human apolipoprotein A-1 not exemplified but capable of forming dimers and/or multimers which retain or improve the pharmacological activities of the ApoA-1Milano mutein known in the literature.

In the present description, by 'multimers' are meant structures comprising three or more monomers, and therefore trimers, tetramers, pentamers, hexamers, up to complex oligomers or polymers. The possibility to form dimers is due to mutations which lead to the presence of at least one cysteine (1C) in the apolipoprotein ApoA-1 mutein chain. The presence of one cysteine allows the formation of a disulfide bridge, and consequently the dimerization of the molecule even in a different point of that typical of ApoA-1Milano. The possibility to form trimers is due to mutations which lead to the presence of at least two cysteines (2C) in the apolipoprotein ApoA-1 mutein chain. For the formation of trimers, it will be necessary to combine 1C molecules and 2C molecules in an adequate stoichiometric ratio. When at least two cysteines per monomer will be present, it will be possible to have different combinations allowing the formation of multimers, starting from tetramers up, reaching to the formation of polymers.

Finally, the expression cassette will contain a polyadenylation signal that may, e.g., derive from the genes of prolamin, glutelins, or globulins mentioned above, or from the terminator of the *Agrobacterium* NOS gene.

The elements that constitute the expression cassette described above need to be functionally bonded in the order listed above, in the direction 5'->3'. The nucleotide sequences coding for the promoters, the signal sequences and the polyadenylation sequences can be arranged in the expression cassette in a "mix" way, i.e. promoter, signal sequence and polyadenylation sequence belonging to different genes (e.g., prolamin promoter, glutelin leader and globulin polyadenylation sequence, etc.) or the above-indicated regulation elements belonging to the same gene (e.g., all from the prolamin gene, all from the glutelin gene, all from the globulin gene, etc.) may be inserted in the cassette.

The expression cassette will be inserted in a suitable vector for the transformation of plants, which could be any known vector suitable for the transformation of plant cells, with the *agrobacterium* method or with physical methods, and for the expression of protein products in plant cells. Said vector can be cut in more suitable restriction sites, and an expression cassette can be inserted in it as described above. An exemplary list of suitable vectors is laid open in the vector-related section, in the description of WO2008/017906.

The plant capable of producing seeds from which to extract the plant milk for the composition according to the present invention can therefore be obtained by transforming or transfecting plant cells with recombinant vectors containing the expression cassette as described, and by selecting the cells transformed or transfected that express the protein. The transformed cells can be selected by selection markers commonly known in the state of the art. The transformed plant cells selected can therefore be induced to regenerate whole, fertile plants capable of producing seeds expressing the apolipoproteins of interest in an essentially dimeric or multimeric active form, following agrotechnical methods known in the specific sector. By way of a non-limiting example, the transformation of the plant cells from which the plant is regenerated can be carried out with cells of *Agrobacterium* containing the expression vector introduced after having rendered them competent by electroporation. The strain with the vector is then used for transforming calli produced by mature embryos or cotyledons. From the calli formed in the presence of the antibiotic used for selection it is induced the forming first of sprouts, and then of roots. Then a stable genetically transformed plant can be selected, whose genetic information, introduced following the transformation, is possibly present in a single copy and expressed, without showing gene silencing phenomena, in successive generations.

According to what described in WO2008/017906, the mutein of apolipoprotein produced as described therein and as reported above will be in the dimeric and/or multimeric form at least in 85% of the apolipoproteins present in the seed, preferably greater than or equal to 90%, more preferably greater than or equal to 95% and even more preferably greater than or equal to 98%.

According to one embodiment of the invention, the muteins in the composition as described above are administered orally to patients in a daily dosage of from 0.2 to 3 mg/kg of body weight; in particular, the muteins can be administered orally to patients in a daily dosage of from 0.4 to 2 mg/kg of body weight; preferably, they will be administered orally to patients in a daily dosage of from 0.5 and 1.8 mg/kg of body weight, and even more preferably they will be administered orally to patients in a daily dosage of from 0.5 to 1.5 mg/kg of body weight.

As evident from the experimental data reported below and in FIGS. 6 and 7, an administration in vivo of a daily dosage of about 0.6 mg of ApoA-1 mutein/kg of body weight yielded wholly unexpected results. The calculated maximum daily dosage was of 1.5 mg/kg body weight. Despite the administered dosage being at least one-tenth, if not one-fiftieth of that suggested in WO2008/017906, the Authors of the invention have found a therapeutic effect of the composition administered at the reduced regimen indicated, and have surprisingly observed that said effect was detectable on animals that continued feeding ad libitum with a high-fat diet, strongly advised against in cases of cardiovascular diseases, where a real therapeutic effect that slows down or arrests disease progression is to be obtained.

As particularly evident from FIG. 7, administration of ApoA-1Milano muteins through rice milk as described herein significantly reduced the area of atherosclerotic plaques and of lipid content, respectively of 40% and 28%, even in the entire Aortic Arch, the region of the aorta where the incidence of atherosclerotic lesions is mostly observed at this stage of disease in homozygous B6.129P2-Apoe$^{tm1Unc}$/J mice fed a high-fat diet.

Moreover, unexpectedly, administration of rice milk containing the ApoA-1Milano muteins significantly reduced also the number of CD68 marker-positive macrophage cells in the liver of homozygous B6.129P2-Apoe$^{tm1Unc}$/J mice fed a high-fat diet (FIG. 8).

To carry out the present invention, plants with seeds which have an elevated protein content are suitable. Among these, legumes such as soybean and other legumes having said characteristics, known to all plant experts, cereals such as rice, oats, barley, spelt, soft wheat, durum wheat, maize, and other cereals that have seeds with high protein content, and also tobacco, are particularly suitable. In these plants, in fact, the protein content in the seeds is about 25-35% in legume seeds, about 10-15% in cereals, and about 20% in tobacco. Of particular importance is also the lipid content that shall preferably be minimal in order not to complicate the purification of apolipoprotein when said purification is desired.

According to one embodiment, therefore, the plants from which seeds the milk for the composition as described above is obtained is a leguminous plant, a cereal or tobacco. In particular, said plant may be selected from the group comprising: rice, corn, wheat, hard (durum) or soft wheat, oats, spelt, barley, soybean, pea, bean, tobacco.

As highlighted by the experimental data described in the Examples section and by the figures, the seed milk used for the composition and the therapeutic method described herein may be fresh, lyophilized, resuspended. In fact, steps of lyophilizing and resuspending in suitable buffers or water did not modify the effectiveness of the muteins Apo present in the milk itself. Therefore, the milk extracted from the seeds of the above-described plants could be used in a fresh, lyophilized, resuspended form and, accordingly, the composition according to the present description could be made in the form of powder, tablet, capsule, hard or soft gelatin, syrup, spray, suspension, milk, solution.

Since the composition must be administered in known daily dosages, which will be calculated based on the body weight of the patient to be treated, it could be implemented in forms enabling an easy metering of the suitable amount to be used. The composition could, e.g., be implemented in submultiples of daily dosages, so as to enable administration of the daily total needed in a single administration or in plural daily administrations.

Together with the composition, there could be provided devices enabling an easy metering of the suitable daily dose, commonly used in the formulations administered in the form of amount of active principle/kg of body weight of the patient.

According to the present description, the composition of the invention could be made, with the appropriate excipients, in the form of pharmaceutical composition, of food supplement, of medical device according to any one of the classes described in Directive 93/42/EEC on medical devices (comprising also substances and not only "devices" in the mechanical sense of the term), or of medical food.

According to one embodiment, the composition as described above, with the dosage regimen as described above, could be used for the treatment of atherosclerosis. As mentioned above and as demonstrated by the experimental data obtained, the composition could be advantageously used also with that class of patients who for any reason, psychological, financial, social, work- or family-related, or a mix thereof, are unable to modify their dietary habits. In particular, the composition could be used for the treatment of atherosclerosis.

As mentioned above, the invention also relates to a method for the treatment of atherosclerosis by oral administration, to a patient in need thereof, of a composition comprising one or more muteins of apolipoprotein A1 (ApoA-1) in the dimeric and/or multimeric form, wherein said muteins are produced in the dimeric and/or multimeric form in plant seeds, said composition comprising milk extracted from seeds of said plants and/or derivatives thereof and wherein said muteins are administered in a daily dosage of from 0.2 and 4 mg/kg of body weight.

What has been described hereto applies, mutatis mutandis, to the therapeutic method.

The following examples are meant to provide a more detailed description of the invention, without however limiting thereto the claimed object.

EXAMPLES

Example 1

Production of Seed Milk and Assessment of Stability of in-Plant Produced Apo A-1 Milano Protein.

a. Rice

Rice milk was obtained from seeds of transgenic lines of rice produced as described above and in WO2008/017906. At ripeness, the seed was harvested, dehusked with a laboratory rice sampling cone (G150/R, Colombini). Cleaned seed was milled with a stone grinding mill until obtaining a flour with particles capable of forming a suspension in water. Flour was resuspended, in the amount of 10%, in water, and the suspension heated to 90° C. for 30 minutes in the presence of amylase to foster saccharification. Upon ending the saccharification process, rice milk was stored at 4° C. and the stability of the ApoA-1Milano protein present was evaluated at 2-day intervals from time 0 (preparation end) to time 6 (+15 days). The protein proved stable throughout the testing period, as demonstrated by the presence of a majority band at 56.000 Da of a Western, performed after SDS-PAGE, of total proteins extracted from the milk. Estimated ApoA-1Milano concentration in rice milk can on average range from 3.5 to 7 mg per liter of milk, prepared as above, depending on transgene expression level. Apolipoprotein concentration can be remarkably increased by using, in lieu of the rice flour, a rice total protein extract, e.g., at 40, 50, 60 or 70% of proteins.

b. Soybean.

Soybean milk is obtained from 100 g of soybean seeds, using 1.2 L of water. Seeds are milled, and concomitantly water is brought to 80° C. for 10 minutes, then increased to 100° C. for 5 minutes. The milk so obtained is filtered to eliminate okara (solid residue of seeds). A milk with a protein content equal to 8.3% is obtained, comparable to a marketed one. Specifically, the Inventors used an automatic soymilk maker (more precisely, SoyQuick)

2. Experiments In Vitro and In Vivo with Rice Seed Milk Produced as Described in Patent Application WO2008/017906

The administration of dimers of anti-atherogenic ApoA-1 muteins to cells and animals was carried out by using milk derived from genetically modified rice plants which express dimers and/or multimers (depending on the number of Cys introduced in the chain) of ApoA-1 muteins in the seeds, as taught in Patent Application WO2008/017906. The ApoA-1 proteins produced in seeds and administered to cells and animals are therefore comprised of the entire-length protein, mutagenized (by Ala-Cys mutations) in order to increase the ability thereof to form dimers or multimers.

The effectiveness of the administration method was assayed in an in vitro model of cultured macrophages exposed to oxidized LDLs (oxLDL, phase 1), then a possible toxicity and tolerability of the administration method was assayed in healthy mice (phase 2). Finally, the effectiveness of the dimers/multimers of ApoA-1 muteins, administered directly in rice milk obtained from the seeds of plants produced as taught in Patent Application WO2008/017906 (APO milk), was assayed in mice model of early atherosclerotic disease (phase 3).

The effectiveness of rice milk obtained from seeds of plants modified as taught in Patent Application WO2008/

017906 in providing functional ApoA-1 muteins (in the dimeric and/or multimeric form, depending on the number of mutations introduced in the WT ApoA-1 protein) to the cells was evaluated by using the THP-1 (ATCC® TIB-202™) cell line, which is a line of cultured monocytes that can be induced to differentiate into macrophages in vitro. In the vascular system of an organism, the monocytes/macrophages in the vessels are the main cells involved in early atheroma pathogenesis. They are in fact activated to phagocytize LDL particles, which are then accumulated inside these cells, leading to degenerative processes typical of atheroma formation. THP-1 cells represent a reliable experimental model to verify the molecular activation of these cells by toxic stimuli such as exposure to oxLDL.

THP-1s differentiated into macrophages were treated with oxLDL alone, or with recombinant ApoA-1 as control, or with rice milk modified as described in Patent Application WO2008/017906, containing therefore dimers/multimers of ApoA-1 muteins (in brief also referred to as Apo-milk in the text). Apo and milk were added after 2 hours of incubation with oxLDL. Controls were added with an equal volume of phosphate-buffered saline (PBS) or with an equal volume of WT milk, and then MCP-1 expression was evaluated, MCP-1 being a cytokine with chemotactic activity (chemokine) involved in monocyte recruitment at the lesion site, and a macrophage activation marker. Apo-milk administration to oxLDL-treated macrophages completely abolished induction of MCP-1 expression, thereby demonstrating that the dimeric/multimeric muteins of ApoA-1 carried in the rice milk effectively reached macrophages and effectively reduced oxLDL-induced activation in these cells (FIG. 1). Apo-milk administration proved even more effective than the administration of recombinant ApoA-1 molecules to the same cells.

The protective effects of Apo-milk in terms of MCP-1 inhibition proved to be dose-dependent (FIG. 2) and were not specific for the sole ApoA-1Milano mutein (dimer). In fact, the administration method proved effective in the inhibition of MCP-1 expression in oxLDL-treated macrophages even when other muteins of ApoA-1 in dimeric/multimeric form were administered, in rice milk modified as described in Patent Application WO2008/017906 (FIG. 3). The milk derived from the same WT rice variety, containing no ApoA-1 molecule, had no noteworthy effects on oxLDL-induced MCP-1 expression, as evidence that the method does not interfere per se with the functionality of the molecules carried (FIG. 3).

To verify whether the administration method were also capable of reducing the anomalous accumulation of lipids by macrophages, which is a typical characteristic of atherosclerotic pathogenesis and progression, differentiated macrophages were exposed to oxLDL, then treated with recombinant ApoA-1, WT rice milk, or various rice milks containing dimers/multimers of ApoA-1 muteins extracted from seeds produced as described in Patent Application WO2008/017906, then lipid accumulation was measured by Oil Red O staining assay. Only ApoA-1 muteins administered in rice milk were able to completely abolish lipid accumulation (FIG. 4), demonstrating that this administration method is capable of protecting macrophages from toxicity induced by exposure to oxLDL.

Apo-milk toxicity was also evaluated, by an assay in healthy mice. A mice group received milk derived from the wild-type rice, whereas a second group of mice received Apo-milk. In all cases, mice were treated daily with Apo-milk containing 0.6 mg/Kg of body weight of ApoA-1Milano mutein produced from seeds of plants modified as taught in WO2008/017906, for 3 weeks, 5 days per week. At the end of the treatment, mice were sacrificed and blood was sampled for analysis. No renal or hepatic toxicity was associated with the treatment, and no sign of inflammation was found in mice treated with rice milk, compared to reference values in untreated mice having the same genetic background (S. C. Grubb, C. J. Bult, M. A. Bogue, Mouse phenome database, Nucleic Acids Res. 42 (2014) D825-34, and FIG. 5).

The method of administration of ApoA-1 muteins through rice milk, with a daily dosage of about 0.6 mg/Kg of body weight of muteins of ApoA-1Milano produced from seeds of plants modified as taught in WO2008/017906, also caused the significant reduction of atherosclerotic disease progression and of aberrant accumulation of lipids in the arterial wall of atherosclerotic mice. Homozygous B6.129P2-Apoe$^{tm1Unc}$/J mice (which is a gene ApoE knockout mice model, prone to incidence of atherosclerotic disease), were fed a high-fat diet (western diet, Mucedola srl, Settimo Milanese, MI, Italy) for 56 days, in order to develop early atherosclerosis (Jeon U S, Choi J-P, Kim Y-S, et al (2015) The enhanced expression of IL-17-secreting T cells during the early progression of atherosclerosis in ApoE-deficient mice fed on a western-type diet. Exp Mol Med. doi: 10.1038/emm.2015.19; Gandhi C, Khan M M, Lentz S R, Chauhan A K (2012) ADAMTS13 reduces vascular inflammation and the development of early atherosclerosis in mice. Blood 119:2385-2391. doi: 10.1182/blood-2011-09-376202; Watt V, Chamberlain J, Steiner T, et al (2011) TRAIL attenuates the development of atherosclerosis in apolipoprotein E deficient mice. Atherosclerosis 215:348-354. doi: 10.1016/j.atherosclerosis.2011.01.010). After 56 days, mice were randomized into two groups (n. 8 each) and treated with a daily administration, by oral gavage, of rice milk produced from seeds of plants mutagenized as described in Patent Application WO2008/017906, which produce ApoA-1 muteins directly in dimeric/multimeric form in seed, or with WT rice milk for 3 weeks, 5 days per week. Daily dosage was of about 0.6 mg Apo A-1Milano mutein/kg of body weight. The high-fat western diet was protracted ad libitum throughout the experiments. At the end of the treatments, animals were sacrificed and organs collected for histologic and lipid accumulation analysis. ApoA-1 muteins administration through rice milk significantly reduced the area of the atherosclerotic plaques detected in the aortic sinuses of mice treated with the above-described dosage regimen of Apo-milk, compared to mice treated with WT-milk, even though mice continued to receive the high-fat diet (FIG. 6). Moreover, digital quantification of Oil Red O-incubated sections, an assay enabling to evaluate the measure of lipid accumulation inside cells and tissues, demonstrated that Apo-milk administration reduced the amount of lipids in the arterial wall in treated mice, compared to control ones who had received wild-type rice milk (FIG. 6).

Moreover, as reported in FIG. 7, ApoA-1Milano muteins administration through rice milk significantly reduced the area of atherosclerotic plaques and of lipid content, respectively of 40% and 28%, even in the entire aortic arch, the region of aorta where the onset of atherosclerotic plaque is most frequently observed at this stage of disease in homozygous B6.129P2-Apoe$^{tm1Unc}$/J mice fed a high-fat diet.

Unexpectedly, finally, administration of rice milk containing the ApoA-1Milano muteins significantly reduced also the number of CD68 marker-positive macrophage cells in the liver of homozygous B6.129P2-Apoe$^{tm1Unc}$/J mice fed a high-fat diet (FIG. 8).

3. Materials and Methods

3.1 Rice Milk.

The rice milk used was provided as lyophilized powder from Plantechno Srl (Vicomoscano, (CR), Italy). The genetically modified rice milk (APO) was produced as indicated in Patent Application WO2008/017906 and reported above in Example 1. WT rice milk of the same variety (Rosa-Marchetti) was used as control. For in vitro experiments, rice milk was handled under sterile conditions, lyophilized and resuspended at a concentration of 2.5 g/ml in phosphate-buffered saline (PBS) and additioned with Zell-Shield (Minerva Biolabs). For in vivo experiments, rice milk was resuspended at a concentration of 2.5 g/ml in sterile water.

3.2 Macrophage/Monocyte Model In Vitro.

THP-1 monocytes were cultivated in a suspension in RPMI 1640 medium added with 10% fetal bovine serum (Euroclone, heat-inactivated), 100 U/ml penicillin and 100 µg/ml streptomycin. All cells were kept in an incubator at 37° C. with 5% $CO_2$. THP-1 monocytes never exceeded the concentration of $1*10^6$ cells/ml.

THP-1 differentiation into macrophages was performed by adding phorbol 12-myristate 13-acetate (PMA) 50 ng/ml and 50 mM β-mercaptoethanol for 48 hours. When indicated, cells received oxLDL (BioTechne, 100 ug/ml) throughout the treatment (6 hours). Rice milk (WT or Apo) or recombinant ApoA-1 protein (Sigma-Aldrich) was added after 2 hours of incubation with oxLDL. Controls were added with an equal volume of phosphate-buffered saline (PBS).

3.3 Cell Lysis, Protein Extracts and Immunoblotting.

At the end of the treatments, THP-1 macrophages were mechanically removed from the plate surface with a scraper. Collected cells were lysed with a modified RIPA buffer: TrisHCl 50 mM, NaCl 500 mM, EDTA 1 mM, EGTA 1 mM, DTT 1 mM, protease inhibitor cocktail (Sigma Aldrich), phosphatase inhibitor (cocktail #2 and #3, Sigma Aldrich). Total protein extracts were quantitated by Bradford test (Sigma Aldrich), following the producer's instructions. The protein extracts were treated to be loaded on NuPAGE Bis-Tris mini gel (Life Technologies) according to the producer's instructions. Nitrocellulose membrane blotting (Life Technologies) was performed by using iBlot System 2 (Life Technologies).

After blocking, the membranes were incubated with the selected primary antibody and then with the appropriate secondary antibody. The Super Signal West Dura Extended Duration Substrate (Thermo Scientific) was added to the membranes, and the chemoluminescent signal digitally acquired by GBox (Syngene). Primary antibodies used were: anti-MCP-1 (mouse monoclonal, [1F10], Sigma-Aldrich), anti-GAPDH (mouse monoclonal, [GAPDH-71.1], Sigma-Aldrich). The secondary antibody used were: Sheep anti-mouse IgG ECL antibody, horseradish peroxidase-conjugated (GE Healthcare).

3.4 In Vitro Oil Red O Staining.

At the end of the treatments, cells were fixed in 10% formalin. After washing, cells were incubated with 60% isopropanol and then left to dry. Oil Red O (0.35% w/v in isopropanol, filtered) was applied to fixed cells. At the end of the incubation, cells were washed with dd$H_2O$. Images were then acquired at the inverted-light microscope (Motic) using an optical camera (Motic). Five independent experiments were carried out, and at least five fields per well were acquired. The images were then quantitated by using the ImageJ program (Schneider C A, Rasband W S, Eliceiri K W. NIH Image to ImageJ: 25 years of image analysis. Nat Methods. 2012; 9:671-5). Red threshold was set and applied to all images.

3.5 In Vivo Studies.

All experiments on animals were carried out in accordance with the Italian Law (Legislative Decree 26/2014) and the European Union Directive (2010/63/EU) on the use of animals in experimentation, further to a protocol approved by the Italian Ministry of Health (Project 08/2014, Authorization N° 202/2015-PR). For the tolerability study, 8-10-week-old male B6 mice were used (Charles River, Calco, LC, Italy). At days 0, mice were randomized and subjected to an oral administration with the WT or Apo rice milk (10 ml/kg, 5 days per week) for 15 days. At the end of the treatments, a blood sample was collected for each animal and, after perfusion, liver and kidneys were collected.

Hematological analyses were performed at the laboratory supporting the animal breeding department of the University of Studies of Milan-Bicocca.

For the effectiveness study, 8-10 weeks-old male B6.129P2-Apoe$^{tm1Unc}$/J mice were fed the western diet (Mucedola Srl, Settimo Milanese (MI), Italy) for 56 days ad libitum. For 56 days, mice were randomized into two groups (n=8) and rice milk (respectively, Apo or WT) was administered to them for 15 days, by gastric gavage. The western diet was maintained ad libitum throughout the experiments. At the end of the treatments, the animals were sacrificed, perfused and various organs were collected.

3.6 Histology Experiments.

Hearts were fixed and cryoconserved (30% sucrose). Heart apex was removed, samples were immersed in OCT (Sakura Finetek OCT) and immediately frozen. Tissues were stored at −80° C., until they were cut using a cryostat. Slides were subsequently incubated with hematoxylin/eosin. For Oil Red O analyses, cryosectioned sections of aortic sinuses were immersed in 1,2-propandiol and then incubated with Oil Red O (0.5% w/v in 1,2-propandiol, filtered). The slides were then washed and mounted with an aqueous mounting medium.

All slides were then digitalized by slide scanner ScanScope (Aperio). Quantification area and signal were performed by using Imagescope (Aperio).

6.7 Immunohistochemistry Experiments.

Livers were collected and fixed in a 4% paraformaldehyde solution. Tissues were then included in paraffin and processed for microtome cutting according to standard procedures. Liver sections were subsequently deparaffined and rehydrated with subsequent steps in an alcohol concentration scale. Sections were then subjected to antigen unmasking by incubation at 95° C. in a citrate sodium solution at pH 6 (H-3300, Vector Laboratories). The sections were then incubated with a 3% $H_2O_2$ solution and processed for immunohistochemistry by using the commercial kits Imm PRESS (Vector Laboratories) and Imm PACT DAB (Vector Laboratories). The sections were then counterstained with Gill hematoxylin and the coverslip was mounted by the solution VectaMount Permanent Mounting Medium (Vector Laboratories). The anti-CD68 primary antibody used, at a concentration of 1:300, was purchased from Abcam (ab125212).

The slides were observed under Nikon Eclipse Ni-U microscope, digital images were acquired by a Nikon DS-Fi1c camera (Nikon, Tokyo, Japan) mounted on the microscope. Therefore, for each section at least 8 different fields were analyzed, and the cells positive and negative to CD68 signal were counted for each field.

6.8 Aortic Arch Analysis.

The entire aorta was collected and stored in a 4% paraformaldehyde solution. The analysis procedure of the aortas was carried out according to a previously described protocol [Beattie J H, Duthie S J, Kwun I S, Ha T Y, Gordon M J. Rapid quantification of aortic lesions in apoE(−/−)

mice. J Vasc Res 2009; 46:347-352]. The aortas, upon removing the perivascular adventitia, were opened longitudinally by and incision and washed in distilled water and 70% 2-propanol. Then, the aortas were incubated with Oil Red O, placed on a black surface and photographed with a Sony A3000 digital photo camera. The images were then processed by the software ImageJ [C. A. Schneider, W. S. Rasband, K. W. Eliceiri, NIH Image to ImageJ: 25 years of image analysis, Nat. Methods 9 (2012) 671-675] and the plaque expressed as percent of the total area of the Aortic Arch. The Aortic Arch was then subdivided from the remainder of the aorta, and the absorbed dye dissolved in chloroform/methanol (2:1 v/v) under continuous stirring. Oil Red O concentration was then measured by a microplate reader (BioTek Instruments, USA) at 520 nm and compared with a standard concentration curve.

Sequence Description

Even-numbered sequences 2 to 38 respectively represent muteins of human protein ApoA1 as reported in sequence 40 below, previously described in WO2008/017906:

```
                                                  SEQ ID 40
Asp Glu Pro Pro Gln Ser Pro Trp Asp Arg Val Lys

Asp Leu Ala Thr Val Tyr Val Asp Val Leu Lys Asp

Ser Gly Arg Asp Tyr Val Ser Gln Phe Glu Gly Ser

Ala Leu Gly Lys Gln Leu Asn Leu Lys Leu Leu Asp

Asn Trp Asp Ser Val Thr Ser Thr Phe Ser Lys Leu

Arg Glu Gln Leu Gly Pro Val Thr Gln Glu Phe Trp

Asp Asn Leu Glu Lys Glu Thr Glu Gly Leu Arg Gln

Glu Met Ser Lys Asp Leu Glu Glu Val Lys Ala Lys

Val Gln Pro Tyr Leu Asp Asp Phe Gln Lys Lys Trp

Gln Glu Glu Met Glu Leu Tyr Arg Gln Lys Val Glu

Pro Leu Arg Ala Glu Leu Gln Glu Gly Ala Arg Gln

Lys Leu His Glu Leu Gln Glu Lys Leu Ser Pro Gly

Glu Glu Met Arg Asp Arg Ala Arg Ala His Val Asp

Ala Leu Arg Thr His Leu Ala Pro Tyr Ser Asp Glu

Leu Arg Gln Arg Leu Ala Ala Arg Leu Glu Ala Leu

Lys Glu Asn Gly Gly Ala Arg Leu Ala Glu Tyr His

Ala Lys Ala Thr Glu His Leu Ser Thr Leu Ser Glu

Lys Ala Lys Pro Ala Leu Glu Asp Leu Arg Gln Gly

Leu Leu Pro Val Leu Glu Ser Phe Lys Val Ser Phe

Leu Ser Ala Leu Glu Glu Tyr Thr Lys Lys Leu Asn

Thr Gln
```

Even-numbered sequences 2 to 38 correspond to SEQ ID 40 with the mutations indicated hereinafter:

SEQ ID 2 Mutation R173C; SEQ ID 4 Mutation R123C; SEQ ID 6 Mutation R215C; SEQ ID 8 Mutation R173C-R215C; SEQ ID 10 Mutation R123C-R215C; SEQ ID 12 Mutation R10C; SEQ ID 14 Mutation R61C; SEQ ID 16 Mutation R83C, SEQ ID 18 Mutation R151C; SEQ ID 20 Mutation R10C-R215C; SEQ ID 22 Mutation R61C-R173C; SEQ ID 24 Mutation R61C-R215C; SEQ ID 26 Mutation R61C-R151C; SEQ ID 28 Mutation R83C-R173C; SEQ ID 30 Mutation R83C-R151C; SEQ ID 32 Mutation R83C-R215C; SEQ ID 34 Mutation R151C-R173C; SEQ ID 36 Mutation R151C-R215C; SEQ ID 38 Mutation R10C-R173C.

Odd-numbered sequences 1 to 39 are examples of nucleotide sequences coding, respectively, for even-numbered sequences 2 to 38 and for sequence 40.

The invention claimed is:

1. A method of treating atherosclerosis comprising orally administering to a patient in need thereof a composition comprising one or more muteins of apolipoprotein 1 selected from the group of consisting of: SEQ ID NO: 2, 4, 6, 8, 10, 12, 14, 16, 18, 20, 22, 24, 26, 28, 30, 32, 34, 36, and 38, in dimeric and/or multimeric form, and are produced in dimeric and/or in multimeric form in plant seeds, said composition further comprising milk extracted from seeds of said plants and/or derivatives thereof, and wherein said composition is administered at a daily dosage of 0.2 to 4 mg/kg of body weight.

2. The method of claim 1, wherein said composition is administered orally to patients at a daily dosage of from 0.4 to 3 mg/kg of body weight.

3. The method of claim 2, wherein said composition is administered orally to patients at a daily dosage of from 0.5 to 2 mg/kg of body weight.

4. The method of claim 3, wherein said composition is administered orally to patients at a daily dosage of from 0.5 to 1.8 mg/kg of body weight.

5. The method of claim 4, wherein said composition is administered orally to patients at a daily dosage of from 0.5 to 1.5 mg/kg of body weight.

6. The method of claim 1, wherein said plant is a leguminous plant, a cereal or tobacco.

7. The method of claim 1, wherein said plant is selected from the group consisting of: rice, corn, wheat, hard (durum) or soft wheat, oats, spelt, barley, soybean, pea, bean, and tobacco.

8. The method of claim 1, wherein said composition is in the form of a powder, tablet, capsule, hard or soft gelatin, syrup, spray, suspension, milk, or solution.

9. The method of claim 8, wherein said milk is in a liquid, lyophilized form, or re-suspended in a suitable carrier.

10. The method of claim 1, wherein said composition is in the form of pharmaceutical composition, a food supplement, medical device or food for special medical purposes.

11. The method of claim 1, wherein the composition comprises an apolipoprotein mutein containing one cysteine amino acid residue and an apolipoprotein mutein with two cysteine residues.

* * * * *

SEQUENCE LISTING

```
<160> NUMBER OF SEQ ID NOS: 40

<210> SEQ ID NO 1
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 Muteine R173C: human Apo A-1 Milano

<400> SEQUENCE: 1 gat gaa ccc ccc cag agc ccc tgg gat cga gtg aag gac ctg gcc act      48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc     192
Asn Trp Asp Ser Val Thr Ser Thr Phe Ser Lys Leu Arg Glu Gln Leu
    50                  55                  60 ggc cct gtg acc cag gag ttc tgg gat aac ctg gaa aag gag aca gag     240
```

```
Gly Pro Val Thr Gln Glu Phe Trp Asp Asn Leu Glu Lys Glu Thr Glu
 65                  70                  75                  80 ggc ctg agg caa gag atg agc aag gat ctg gag gag gtg aag gcc aag    288
Gly Leu Arg Gln Glu Met Ser Lys Asp Leu Glu Glu Val Lys Ala Lys
                 85                  90                  95 gtg cag ccc tac ctg gac gac ttc cag aag aag tgg cag gag gag atg    336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag    384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg    432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc    480
Gly Glu Glu Met Arg Asp Arg Ala Arg Ala His Val Asp Ala Leu Arg
145                 150                 155                 160 acg cat ctg gcc ccc tac agc gac gag ctg cgc cag tgc ttg gcc gcg    528
Thr His Leu Ala Pro Tyr Ser Asp Glu Leu Arg Gln Cys Leu Ala Ala
                165                 170                 175 cgc ctt gag gct ctc aag gag aac ggc ggc gcc aga ctg gcc gag tac    576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag    624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc    672
Pro Ala Leu Glu Asp Leu Arg Gln Gly Leu Leu Pro Val Leu Glu Ser
    210                 215                 220 ttc aag gtc agc ttc ctg agc gct ctc gag gag tac act aag aag ctc    720
Phe Lys Val Ser Phe Leu Ser Ala Leu Glu Glu Tyr Thr Lys Lys Leu
225                 230                 235                 240 aac acc cag tga                                                    732
Asn Thr Gln <210> SEQ ID NO 2
<211> LENGTH: 243
<212> TYPE: PRT
<213> ORGANISM: Homo sapiens

<400> SEQUENCE: 2

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
```

```
                    130                 135                 140
Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 3
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R123C

<400> SEQUENCE: 3 gat gaa ccc ccc cag agc ccc tgg gat cga gtg aag gac ctg gcc act       48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag       96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac      144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc      192
Asn Trp Asp Ser Val Thr Ser Thr Phe Ser Lys Leu Arg Glu Gln Leu
    50                  55                  60 ggc cct gtg acc cag gag ttc tgg gat aac ctg gaa aag gag aca gag      240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag      288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg      336
Val Gln Pro Tyr Leu Asp Asp Phe Gln Lys Lys Trp Gln Glu Glu Met
            100                 105                 110 gag ctc tac cgc cag aag gtg gag ccg ctg tgc gca gag ctc caa gag      384
Glu Leu Tyr Arg Gln Lys Val Glu Pro Leu Cys Ala Glu Leu Gln Glu
        115                 120                 125 ggc gcg cgc cag aag ctg cac gag ctg caa gag aag ctg agc cca ctg      432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc      480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg      528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac      576
```

Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag    624
His Ala Lys Ala Thr Glu His Leu Ser Thr Leu Ser Glu Lys Ala Lys
            195                 200                 205 ccc gcg ctc gag gac ctc cgc caa ggc ctg ctg ccc gtg ctg gag agc    672
Pro Ala Leu Glu Asp Leu Arg Gln Gly Leu Leu Pro Val Leu Glu Ser
210                 215                 220 ttc aag gtc agc ttc ctg agc gct ctc gag gag tac act aag aag ctc    720
Phe Lys Val Ser Phe Leu Ser Ala Leu Glu Glu Tyr Thr Lys Lys Leu
225                 230                 235                 240 aac acc cag tga                                                    732
Asn Thr Gln <210> SEQ ID NO 4
<211> LENGTH: 243
<212> TYPE: PRT
<213> ORGANISM: Homo sapiens

<400> SEQUENCE: 4

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Cys Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 5
<211> LENGTH: 732
<212> TYPE: DNA
<213> ORGANISM: Homo sapiens
<220> FEATURE:

<220> NAME/KEY: CDS
<222> LOCATION: (1)..(732)
<223> OTHER INFORMATION: Apo A-1 human mutein R215C

<400> SEQUENCE: 5

```
gat gaa ccc ccc cag agc ccc tgg gat cga gtg aag gac ctg gcc act      48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc     192
Asn Trp Asp Ser Val Thr Ser Thr Phe Ser Lys Leu Arg Glu Gln Leu
 50                  55                  60 ggc cct gtg acc cag gag ttc tgg gat aac ctg gaa aag gag aca gag     240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag     288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg     336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag     384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg     432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc     480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg     528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac     576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag     624
His Ala Lys Ala Thr Glu His Leu Ser Thr Leu Ser Glu Lys Ala Lys
        195                 200                 205 ccc gcg ctc gag gac ctc tgc caa ggc ctg ctg ccc gtg ctg gag agc     672
Pro Ala Leu Glu Asp Leu Cys Gln Gly Leu Leu Pro Val Leu Glu Ser
    210                 215                 220 ttc aag gtc agc ttc ctg agc gct ctc gag gag tac act aag aag ctc     720
Phe Lys Val Ser Phe Leu Ser Ala Leu Glu Glu Tyr Thr Lys Lys Leu
225                 230                 235                 240 aac acc cag tga                                                     732
Asn Thr Gln
```

<210> SEQ ID NO 6
<211> LENGTH: 243
<212> TYPE: PRT
<213> ORGANISM: Homo sapiens

<400> SEQUENCE: 6

```
Asp Glu Pro Pro Gln Ser Pro Trp Asp Arg Val Lys Asp Leu Ala Thr
1               5                   10                  15
```

```
Val Tyr Val Asp Val Leu Lys Asp Ser Gly Arg Asp Tyr Val Ser Gln
             20                  25                  30

Phe Glu Gly Ser Ala Leu Gly Lys Gln Leu Asn Leu Lys Leu Leu Asp
         35                  40                  45

Asn Trp Asp Ser Val Thr Ser Thr Phe Ser Lys Leu Arg Glu Gln Leu
 50                  55                  60

Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Glu Val Lys Ala Lys
                 85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Cys Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 7
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R173C, R215C

<400> SEQUENCE: 7 gat gaa ccc ccc cag agc ccc tgg gat cga gtg aag gac ctg gcc act    48
Asp Glu Pro Pro Gln Ser Pro Trp Asp Arg Val Lys Asp Leu Ala Thr
1               5                  10                  15 gtg tac gtg gat gtg ctc aaa gac agc ggc aga gac tat gtg tcc cag    96
Val Tyr Val Asp Val Leu Lys Asp Ser Gly Arg Asp Tyr Val Ser Gln
             20                  25                  30 ttt gaa ggc tcc gcc ttg gga aaa cag cta aac cta aag ctc ctt gac   144
Phe Glu Gly Ser Ala Leu Gly Lys Gln Leu Asn Leu Lys Leu Leu Asp
         35                  40                  45 aac tgg gac agc gtg acc tcc acc ttc agc aag ctg cgc gaa cag ctc   192
Asn Trp Asp Ser Val Thr Ser Thr Phe Ser Lys Leu Arg Glu Gln Leu
 50                  55                  60 ggc cct gtg acc cag gag ttc tgg gat aac ctg gaa aag gag aca gag   240
Gly Pro Val Thr Gln Glu Phe Trp Asp Asn Leu Glu Lys Glu Thr Glu
 65                  70                  75                  80 ggc ctg agg caa gag atg agc aag gat ctg gag gag gtg aag gcc aag   288
Gly Leu Arg Gln Glu Met Ser Lys Asp Leu Glu Glu Val Lys Ala Lys
```

```
                          85                   90                    95
gtg cag ccc tac ctg gac gac ttc cag aag aag tgg cag gag gag atg        336
Val Gln Pro Tyr Leu Asp Asp Phe Gln Lys Lys Trp Gln Glu Glu Met
                100                 105                 110 gag ctc tac cgc cag aag gtg gag ccg ctg cgc gca gag ctc caa gag        384
Glu Leu Tyr Arg Gln Lys Val Glu Pro Leu Arg Ala Glu Leu Gln Glu
            115                 120                 125 ggc gcg cgc cag aag ctg cac gag ctg caa gag aag ctg agc cca ctg        432
Gly Ala Arg Gln Lys Leu His Glu Leu Gln Glu Lys Leu Ser Pro Leu
        130                 135                 140 ggc gag gag atg cgc gac cgc gcg cgc gcc cat gtg gac gcg ctg cgc        480
Gly Glu Glu Met Arg Asp Arg Ala Arg Ala His Val Asp Ala Leu Arg
145                 150                 155                 160 acg cat ctg gcc ccc tac agc gac gag ctg cgc cag tgc ttg gcc gcg        528
Thr His Leu Ala Pro Tyr Ser Asp Glu Leu Arg Gln Cys Leu Ala Ala
                165                 170                 175 cgc ctt gag gct ctc aag gag aac ggc ggc gcc aga ctg gcc gag tac        576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag        624
His Ala Lys Ala Thr Glu His Leu Ser Thr Leu Ser Glu Lys Ala Lys
        195                 200                 205 ccc gcg ctc gag gac ctc tgc caa ggc ctg ctg ccc gtg ctg gag agc        672
Pro Ala Leu Glu Asp Leu Cys Gln Gly Leu Leu Pro Val Leu Glu Ser
210                 215                 220 ttc aag gtc agc ttc ctg agc gct ctc gag gag tac act aag aag ctc        720
Phe Lys Val Ser Phe Leu Ser Ala Leu Glu Glu Tyr Thr Lys Lys Leu
225                 230                 235                 240 aac acc cag tga                                                         732
Asn Thr Gln <210> SEQ ID NO 8
<211> LENGTH: 243
<212> TYPE: PRT
<213> ORGANISM: Homo sapiens

<400> SEQUENCE: 8

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
        50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
                100                 105                 110

Glu Leu Tyr Arg Gln Lys Val Glu Pro Leu Arg Ala Glu Leu Gln Glu
            115                 120                 125

Gly Ala Arg Gln Lys Leu His Glu Leu Gln Glu Lys Leu Ser Pro Leu
        130                 135                 140

Gly Glu Glu Met Arg Asp Arg Ala Arg Ala His Val Asp Ala Leu Arg
145                 150                 155                 160
```

```
Thr His Leu Ala Pro Tyr Ser Asp Glu Leu Arg Gln Cys Leu Ala Ala
            165                 170                 175

Arg Leu Glu Ala Leu Lys Glu Asn Gly Gly Ala Arg Leu Ala Glu Tyr
        180                 185                 190

His Ala Lys Ala Thr Glu His Leu Ser Thr Leu Ser Glu Lys Ala Lys
    195                 200                 205

Pro Ala Leu Glu Asp Leu Cys Gln Gly Leu Leu Pro Val Leu Glu Ser
210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 9
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R123C, R215C

<400> SEQUENCE: 9 gat gaa ccc ccc cag agc ccc tgg gat cga gtg aag gac ctg gcc act    48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag    96
Val Tyr Val Asp Val Leu Lys Asp Ser Gly Arg Asp Tyr Val Ser Gln
                20                  25                  30 ttt gaa ggc tcc gcc ttg gga aaa cag cta aac cta aag ctc ctt gac   144
Phe Glu Gly Ser Ala Leu Gly Lys Gln Leu Asn Leu Lys Leu Leu Asp
            35                  40                  45 aac tgg gac agc gtg acc tcc acc ttc agc aag ctg cgc gaa cag ctc   192
Asn Trp Asp Ser Val Thr Ser Thr Phe Ser Lys Leu Arg Glu Gln Leu
        50                  55                  60 ggc cct gtg acc cag gag ttc tgg gat aac ctg gaa aag gag aca gag   240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag   288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg   336
Val Gln Pro Tyr Leu Asp Asp Phe Gln Lys Lys Trp Gln Glu Glu Met
            100                 105                 110 gag ctc tac cgc cag aag gtg gag ccg ctg tgc gca gag ctc caa gag   384
Glu Leu Tyr Arg Gln Lys Val Glu Pro Leu Cys Ala Glu Leu Gln Glu
        115                 120                 125 ggc gcg cgc cag aag ctg cac gag ctg caa gag aag ctg agc cca ctg   432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc   480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg   528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac   576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag   624
His Ala Lys Ala Thr Glu His Leu Ser Thr Leu Ser Glu Lys Ala Lys
```

```
            195                 200                 205
ccc gcg ctc gag gac ctc tgc caa ggc ctg ctg ccc gtg ctg gag agc      672
Pro Ala Leu Glu Asp Leu Cys Gln Gly Leu Leu Pro Val Leu Glu Ser
    210                 215                 220 ttc aag gtc agc ttc ctg agc gct ctc gag gag tac act aag aag ctc      720
Phe Lys Val Ser Phe Leu Ser Ala Leu Glu Glu Tyr Thr Lys Lys Leu
225                 230                 235                 240 aac acc cag tga                                                      732
Asn Thr Gln <210> SEQ ID NO 10
<211> LENGTH: 243
<212> TYPE: PRT
<213> ORGANISM: Homo sapiens

<400> SEQUENCE: 10

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Cys Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Cys Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 11
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R10C

<400> SEQUENCE: 11
```

```
gat gaa ccc ccc cag agc ccc tgg gat tgt gtg aag gac ctg gcc act         48
Asp Glu Pro Pro Gln Ser Pro Trp Asp Cys Val Lys Asp Leu Ala Thr
1               5                   10                  15 gtg tac gtg gat gtg ctc aaa gac agc ggc aga gac tat gtg tcc cag         96
Val Tyr Val Asp Val Leu Lys Asp Ser Gly Arg Asp Tyr Val Ser Gln
                20                  25                  30 ttt gaa ggc tcc gcc ttg gga aaa cag cta aac cta aag ctc ctt gac        144
Phe Glu Gly Ser Ala Leu Gly Lys Gln Leu Asn Leu Lys Leu Leu Asp
            35                  40                  45 aac tgg gac agc gtg acc tcc acc ttc agc aag ctg cgc gaa cag ctc        192
Asn Trp Asp Ser Val Thr Ser Thr Phe Ser Lys Leu Arg Glu Gln Leu
        50                  55                  60 ggc cct gtg acc cag gag ttc tgg gat aac ctg gaa aag gag aca gag        240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag        288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg        336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag        384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg        432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc        480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg        528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac        576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag        624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc        672
Pro Ala Leu Glu Asp Leu Arg Gln Gly Leu Leu Pro Val Leu Glu Ser
    210                 215                 220 ttc aag gtc agc ttc ctg agc gct ctc gag gag tac act aag aag ctc        720
Phe Lys Val Ser Phe Leu Ser Ala Leu Glu Glu Tyr Thr Lys Lys Leu
225                 230                 235                 240 aac acc cag tga                                                         732
Asn Thr Gln <210> SEQ ID NO 12
<211> LENGTH: 243
<212> TYPE: PRT
<213> ORGANISM: Homo sapiens

<400> SEQUENCE: 12

Asp Glu Pro Pro Gln Ser Pro Trp Asp Cys Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
```

```
                35                  40                  45
Asn Trp Asp Ser Val Thr Ser Thr Phe Ser Lys Leu Arg Glu Gln Leu
 50                  55                  60

Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Glu Val Lys Ala Lys
                 85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 13
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R61C

<400> SEQUENCE: 13 gat gaa ccc ccc cag agc ccc tgg gat cga gtg aag gac ctg gcc act    48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag    96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac   144
Phe Glu Gly Ser Ala Leu Gly Lys Gln Leu Asn Leu Lys Leu Leu Asp
        35                  40                  45 aac tgg gac agc gtg acc tcc acc ttc agc aag ctg tgc gaa cag ctc   192
Asn Trp Asp Ser Val Thr Ser Thr Phe Ser Lys Leu Cys Glu Gln Leu
    50                  55                  60 ggc cct gtg acc cag gag ttc tgg gat aac ctg gaa aag gag aca gag   240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag   288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg   336
Val Gln Pro Tyr Leu Asp Asp Phe Gln Lys Lys Trp Gln Glu Glu Met
            100                 105                 110
```

```
gag ctc tac cgc cag aag gtg gag ccg ctg cgc gca gag ctc caa gag      384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg      432
Gly Ala Arg Gln Lys Leu His Glu Leu Gln Glu Lys Leu Ser Pro Leu
130                 135                 140 ggc gag gag atg cgc gac cgc gcg cgc gcc cat gtg gac gcg ctg cgc      480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg      528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac      576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag      624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc      672
Pro Ala Leu Glu Asp Leu Arg Gln Gly Leu Leu Pro Val Leu Glu Ser
210                 215                 220 ttc aag gtc agc ttc ctg agc gct ctc gag gag tac act aag aag ctc      720
Phe Lys Val Ser Phe Leu Ser Ala Leu Glu Glu Tyr Thr Lys Lys Leu
225                 230                 235                 240 aac acc cag tga                                                      732
Asn Thr Gln <210> SEQ ID NO 14
<211> LENGTH: 243
<212> TYPE: PRT
<213> ORGANISM: Homo sapiens

<400> SEQUENCE: 14

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Cys Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190
```

```
His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 15
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R83C

<400> SEQUENCE: 15 gat gaa ccc ccc cag agc ccc tgg gat cga gtg aag gac ctg gcc act    48
Asp Glu Pro Pro Gln Ser Pro Trp Asp Arg Val Lys Asp Leu Ala Thr
1               5                  10                  15 gtg tac gtg gat gtg ctc aaa gac agc ggc aga gac tat gtg tcc cag    96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac   144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc   192
Asn Trp Asp Ser Val Thr Ser Thr Phe Ser Lys Leu Arg Glu Gln Leu
    50                  55                  60 ggc cct gtg acc cag gag ttc tgg gat aac ctg gaa aag gag aca gag   240
Gly Pro Val Thr Gln Glu Phe Trp Asp Asn Leu Glu Lys Glu Thr Glu
65                  70                  75                  80 ggc ctg tgc caa gag atg agc aag gat ctg gag gag gtg aag gcc aag   288
Gly Leu Cys Gln Glu Met Ser Lys Asp Leu Glu Glu Val Lys Ala Lys
                85                  90                  95 gtg cag ccc tac ctg gac gac ttc cag aag aag tgg cag gag gag atg   336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag   384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg   432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc   480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg   528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac   576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag   624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc   672
Pro Ala Leu Glu Asp Leu Arg Gln Gly Leu Leu Pro Val Leu Glu Ser
    210                 215                 220
```

```
ttc aag gtc agc ttc ctg agc gct ctc gag gag tac act aag aag ctc      720
Phe Lys Val Ser Phe Leu Ser Ala Leu Glu Glu Tyr Thr Lys Lys Leu
225                 230                 235                 240 aac acc cag tga                                                       732
Asn Thr Gln
```

<210> SEQ ID NO 16
<211> LENGTH: 243
<212> TYPE: PRT
<213> ORGANISM: Homo sapiens

<400> SEQUENCE: 16

```
Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Cys Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
                100                 105                 110

Glu Leu Tyr Arg Gln Lys Val Glu Pro Leu Arg Ala Glu Leu Gln Glu
            115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
    195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln
```

<210> SEQ ID NO 17
<211> LENGTH: 732
<212> TYPE: DNA
<213> ORGANISM: Homo sapiens
<220> FEATURE:
<221> NAME/KEY: CDS
<222> LOCATION: (1)..(723)
<223> OTHER INFORMATION: Apo A-1 human mutein R151C

<400> SEQUENCE: 17

```
gat gaa ccc ccc cag agc ccc tgg gat cga gtg aag gac ctg gcc act       48
Asp Glu Pro Pro Gln Ser Pro Trp Asp Arg Val Lys Asp Leu Ala Thr
1               5                   10                  15
```

| | | |
|---|---|---|
| gtg tac gtg gat gtg ctc aaa gac agc ggc aga gac tat gtg tcc cag<br>Val Tyr Val Asp Val Leu Lys Asp Ser Gly Arg Asp Tyr Val Ser Gln<br>20                       25                     30 | | 96 |
| ttt gaa ggc tcc gcc ttg gga aaa cag cta aac cta aag ctc ctt gac<br>Phe Glu Gly Ser Ala Leu Gly Lys Gln Leu Asn Leu Lys Leu Leu Asp<br>     35                    40                    45 | | 144 |
| aac tgg gac agc gtg acc tcc acc ttc agc aag ctg cgc gaa cag ctc<br>Asn Trp Asp Ser Val Thr Ser Thr Phe Ser Lys Leu Arg Glu Gln Leu<br>50                       55                     60 | | 192 |
| ggc cct gtg acc cag gag ttc tgg gat aac ctg gaa aag gag aca gag<br>Gly Pro Val Thr Gln Glu Phe Trp Asp Asn Leu Glu Lys Glu Thr Glu<br>65                       70                    75                    80 | | 240 |
| ggc ctg agg caa gag atg agc aag gat ctg gag gag gtg aag gcc aag<br>Gly Leu Arg Gln Glu Met Ser Lys Asp Leu Glu Glu Val Lys Ala Lys<br>                       85                    90                    95 | | 288 |
| gtg cag ccc tac ctg gac gac ttc cag aag aag tgg cag gag gag atg<br>Val Gln Pro Tyr Leu Asp Asp Phe Gln Lys Lys Trp Gln Glu Glu Met<br>                100                   105                  110 | | 336 |
| gag ctc tac cgc cag aag gtg gag ccg ctg cgc gca gag ctc caa gag<br>Glu Leu Tyr Arg Gln Lys Val Glu Pro Leu Arg Ala Glu Leu Gln Glu<br>              115                   120                  125 | | 384 |
| ggc gcg cgc cag aag ctg cac gag ctg caa gag aag ctg agc cca ctg<br>Gly Ala Arg Gln Lys Leu His Glu Leu Gln Glu Lys Leu Ser Pro Leu<br>130                      135                   140 | | 432 |
| ggc gag gag atg cgc gac tgc gcg cgc gcc cat gtg gac gcg ctg cgc<br>Gly Glu Glu Met Arg Asp Cys Ala Arg Ala His Val Asp Ala Leu Arg<br>145                       150                   155                  160 | | 480 |
| acg cat ctg gcc ccc tac agc gac gag ctg cgc cag cgc ttg gcc gcg<br>Thr His Leu Ala Pro Tyr Ser Asp Glu Leu Arg Gln Arg Leu Ala Ala<br>              165                   170                  175 | | 528 |
| cgc ctt gag gct ctc aag gag aac ggc ggc gcc aga ctg gcc gag tac<br>Arg Leu Glu Ala Leu Lys Glu Asn Gly Gly Ala Arg Leu Ala Glu Tyr<br>                 180                   185                  190 | | 576 |
| cac gcc aag gcc acc gag cat ctg agc acg ctc agc gag aag gcc aag<br>His Ala Lys Ala Thr Glu His Leu Ser Thr Leu Ser Glu Lys Ala Lys<br>              195                   200                  205 | | 624 |
| ccc gcg ctc gag gac ctc cgc caa ggc ctg ctg ccc gtg ctg gag agc<br>Pro Ala Leu Glu Asp Leu Arg Gln Gly Leu Leu Pro Val Leu Glu Ser<br>210                      215                   220 | | 672 |
| ttc aag gtc agc ttc ctg agc gct ctc gag gag tac act aag aag ctc<br>Phe Lys Val Ser Phe Leu Ser Ala Leu Glu Glu Tyr Thr Lys Lys Leu<br>225                      230                    235                  240 | | 720 |
| aac acccagtga<br>Asn | | 732 |

<210> SEQ ID NO 18
<211> LENGTH: 241
<212> TYPE: PRT
<213> ORGANISM: Homo sapiens

<400> SEQUENCE: 18

Asp Glu Pro Pro Gln Ser Pro Trp Asp Arg Val Lys Asp Leu Ala Thr
1               5                   10                   15

Val Tyr Val Asp Val Leu Lys Asp Ser Gly Arg Asp Tyr Val Ser Gln
                20                   25                   30

Phe Glu Gly Ser Ala Leu Gly Lys Gln Leu Asn Leu Lys Leu Leu Asp
             35                   40                   45

Asn Trp Asp Ser Val Thr Ser Thr Phe Ser Lys Leu Arg Glu Gln Leu
50                     55                   60

-continued

```
Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Glu Val Lys Ala Lys
                 85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Met Arg Asp Cys Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn
```

<210> SEQ ID NO 19
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R10C, R215C

<400> SEQUENCE: 19

```
gat gaa ccc ccc cag agc ccc tgg gat tgt gtg aag gac ctg gcc act      48
Asp Glu Pro Pro Gln Ser Pro Trp Asp Cys Val Lys Asp Leu Ala Thr
1               5                   10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc     192
Asn Trp Asp Ser Val Thr Ser Thr Phe Ser Lys Leu Arg Glu Gln Leu
    50                  55                  60 ggc cct gtg acc cag gag ttc tgg gat aac ctg gaa aag gag aca gag     240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag     288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg     336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag     384
Glu Leu Tyr Arg Gln Lys Val Glu Pro Leu Arg Ala Glu Leu Gln Glu
        115                 120                 125
```

```
ggc gcg cgc cag aag ctg cac gag ctg caa gag aag ctg agc cca ctg       432
Gly Ala Arg Gln Lys Leu His Glu Leu Gln Glu Lys Leu Ser Pro Leu
130                 135                 140 ggc gag gag atg cgc gac cgc gcg cgc gcc cat gtg gac gcg ctg cgc       480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg       528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac       576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag       624
His Ala Lys Ala Thr Glu His Leu Ser Thr Leu Ser Glu Lys Ala Lys
        195                 200                 205 ccc gcg ctc gag gac ctc tgc caa ggc ctg ctc ccc gtg ctg gag agc       672
Pro Ala Leu Glu Asp Leu Cys Gln Gly Leu Leu Pro Val Leu Glu Ser
210                 215                 220 ttc aag gtc agc ttc ctg agc gct ctc gag gag tac act aag aag ctc       720
Phe Lys Val Ser Phe Leu Ser Ala Leu Glu Glu Tyr Thr Lys Lys Leu
225                 230                 235                 240 aac acc cag tga                                                       732
Asn Thr Gln <210> SEQ ID NO 20
<211> LENGTH: 243
<212> TYPE: PRT
<213> ORGANISM: Homo sapiens

<400> SEQUENCE: 20

Asp Glu Pro Pro Gln Ser Pro Trp Asp Cys Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
        50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
                100                 105                 110

Glu Leu Tyr Arg Gln Lys Val Glu Pro Leu Arg Ala Glu Leu Gln Glu
            115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Cys Gln Gly Leu Leu Pro Val Leu Glu Ser
```

```
                    210                 215                 220
Phe Lys Val Ser Phe Leu Ser Ala Leu Glu Glu Tyr Thr Lys Lys Leu
225                 230                 235                 240

Asn Thr Gln

<210> SEQ ID NO 21
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R61C, R173C

<400> SEQUENCE: 21 gat gaa ccc ccc cag agc ccc tgg gat cga gtg aag gac ctg gcc act      48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
                20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
            35                  40                  45 aac tgg gac agc gtg acc tcc acc ttc agc aag ctg tgc gaa cag ctc     192
Asn Trp Asp Ser Val Thr Ser Thr Phe Ser Lys Leu Cys Glu Gln Leu
        50                  55                  60 ggc cct gtg acc cag gag ttc tgg gat aac ctg gaa aag gag aca gag     240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag     288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg     336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag     384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg     432
Gly Ala Arg Gln Lys Leu His Glu Leu Gln Glu Lys Leu Ser Pro Leu
130                 135                 140 ggc gag gag atg cgc gac cgc gcg cgc gcc cat gtg gac gcg ctg cgc     480
Gly Glu Glu Met Arg Asp Arg Ala Arg Ala His Val Asp Ala Leu Arg
145                 150                 155                 160 acg cat ctg gcc ccc tac agc gac gag ctg cgc cag tgc ttg gcc gcg     528
Thr His Leu Ala Pro Tyr Ser Asp Glu Leu Arg Gln Cys Leu Ala Ala
                165                 170                 175 cgc ctt gag gct ctc aag gag aac ggc ggc gcc aga ctg gcc gag tac     576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag     624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc     672
Pro Ala Leu Glu Asp Leu Arg Gln Gly Leu Leu Pro Val Leu Glu Ser
210                 215                 220 ttc aag gtc agc ttc ctg agc gct ctc gag gag tac act aag aag ctc     720
Phe Lys Val Ser Phe Leu Ser Ala Leu Glu Glu Tyr Thr Lys Lys Leu
225                 230                 235                 240
```

```
aac acc cag tga                                              732
Asn Thr Gln
```

<210> SEQ ID NO 22
<211> LENGTH: 243
<212> TYPE: PRT
<213> ORGANISM: Homo sapiens

<400> SEQUENCE: 22

```
Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Cys Glu Gln Leu
 50                  55                  60

Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln
```

<210> SEQ ID NO 23
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R61C, R215C

<400> SEQUENCE: 23

```
gat gaa ccc ccc cag agc ccc tgg gat cga gtg aag gac ctg gcc act    48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag    96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac   144
```

```
Phe Glu Gly Ser Ala Leu Gly Lys Gln Leu Asn Leu Lys Leu Leu Asp
         35                  40                  45 aac tgg gac agc gtg acc tcc acc ttc agc aag ctg tgc gaa cag ctc      192
Asn Trp Asp Ser Val Thr Ser Thr Phe Ser Lys Leu Cys Glu Gln Leu
 50                  55                  60 ggc cct gtg acc cag gag ttc tgg gat aac ctg gaa aag gag aca gag      240
Gly Pro Val Thr Gln Glu Phe Trp Asp Asn Leu Glu Lys Glu Thr Glu
 65                  70                  75                  80 ggc ctg agg caa gag atg agc aag gat ctg gag gag gtg aag gcc aag      288
Gly Leu Arg Gln Glu Met Ser Lys Asp Leu Glu Glu Val Lys Ala Lys
                 85                  90                  95 gtg cag ccc tac ctg gac gac ttc cag aag aag tgg cag gag gag atg      336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag      384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg      432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc      480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg      528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac      576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag      624
His Ala Lys Ala Thr Glu His Leu Ser Thr Leu Ser Glu Lys Ala Lys
        195                 200                 205 ccc gcg ctc gag gac ctc tgc caa ggc ctg ctg ccc gtg ctg gag agc      672
Pro Ala Leu Glu Asp Leu Cys Gln Gly Leu Leu Pro Val Leu Glu Ser
    210                 215                 220 ttc aag gtc agc ttc ctg agc gct ctc gag gag tac act aag aag ctc      720
Phe Lys Val Ser Phe Leu Ser Ala Leu Glu Glu Tyr Thr Lys Lys Leu
225                 230                 235                 240 aac acc cag tga                                                      732
Asn Thr Gln <210> SEQ ID NO 24
<211> LENGTH: 243
<212> TYPE: PRT
<213> ORGANISM: Homo sapiens

<400> SEQUENCE: 24

Asp Glu Pro Pro Gln Ser Pro Trp Asp Arg Val Lys Asp Leu Ala Thr
  1               5                  10                  15

Val Tyr Val Asp Val Leu Lys Asp Ser Gly Arg Asp Tyr Val Ser Gln
                 20                  25                  30

Phe Glu Gly Ser Ala Leu Gly Lys Gln Leu Asn Leu Lys Leu Leu Asp
             35                  40                  45

Asn Trp Asp Ser Val Thr Ser Thr Phe Ser Lys Leu Cys Glu Gln Leu
 50                  55                  60

Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Glu Val Lys Ala Lys
                 85                  90                  95
```

```
Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Cys Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 25
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R61C, R151C

<400> SEQUENCE: 25
```

| | | | | | | | | | | | | | | | | |
|---|---|---|---|---|---|---|---|---|---|---|---|---|---|---|---|---|
| gat | gaa | ccc | ccc | cag | agc | ccc | tgg | gat | cga | gtg | aag | gac | ctg | gcc | act | 48 |
| Asp | Glu | Pro | Pro | Gln | Ser | Pro | Trp | Asp | Arg | Val | Lys | Asp | Leu | Ala | Thr | |
| 1 | | | | 5 | | | | | 10 | | | | | 15 | | |
| gtg | tac | gtg | gat | gtg | ctc | aaa | gac | agc | ggc | aga | gac | tat | gtg | tcc | cag | 96 |
| Val | Tyr | Val | Asp | Val | Leu | Lys | Asp | Ser | Gly | Arg | Asp | Tyr | Val | Ser | Gln | |
| | | | 20 | | | | | 25 | | | | | 30 | | | |
| ttt | gaa | ggc | tcc | gcc | ttg | gga | aaa | cag | cta | aac | cta | aag | ctc | ctt | gac | 144 |
| Phe | Glu | Gly | Ser | Ala | Leu | Gly | Lys | Gln | Leu | Asn | Leu | Lys | Leu | Leu | Asp | |
| | | 35 | | | | | 40 | | | | | 45 | | | | |
| aac | tgg | gac | agc | gtg | acc | tcc | acc | ttc | agc | aag | ctg | tgc | gaa | cag | ctc | 192 |
| Asn | Trp | Asp | Ser | Val | Thr | Ser | Thr | Phe | Ser | Lys | Leu | Cys | Glu | Gln | Leu | |
| | 50 | | | | | 55 | | | | | 60 | | | | | |
| ggc | cct | gtg | acc | cag | gag | ttc | tgg | gat | aac | ctg | gaa | aag | gag | aca | gag | 240 |
| Gly | Pro | Val | Thr | Gln | Glu | Phe | Trp | Asp | Asn | Leu | Glu | Lys | Glu | Thr | Glu | |
| 65 | | | | | 70 | | | | | 75 | | | | | 80 | |
| ggc | ctg | agg | caa | gag | atg | agc | aag | gat | ctg | gag | gag | gtg | aag | gcc | aag | 288 |
| Gly | Leu | Arg | Gln | Glu | Met | Ser | Lys | Asp | Leu | Glu | Glu | Val | Lys | Ala | Lys | |
| | | | | 85 | | | | | 90 | | | | | 95 | | |
| gtg | cag | ccc | tac | ctg | gac | gac | ttc | cag | aag | aag | tgg | cag | gag | gag | atg | 336 |
| Val | Gln | Pro | Tyr | Leu | Asp | Asp | Phe | Gln | Lys | Lys | Trp | Gln | Glu | Glu | Met | |
| | | | 100 | | | | | 105 | | | | | 110 | | | |
| gag | ctc | tac | cgc | cag | aag | gtg | gag | ccg | ctg | cgc | gca | gag | ctc | caa | gag | 384 |
| Glu | Leu | Tyr | Arg | Gln | Lys | Val | Glu | Pro | Leu | Arg | Ala | Glu | Leu | Gln | Glu | |
| | | | | 115 | | | | | 120 | | | | | 125 | | |
| ggc | gcg | cgc | cag | aag | ctg | cac | gag | ctg | caa | gag | aag | ctg | agc | cca | ctg | 432 |
| Gly | Ala | Arg | Gln | Lys | Leu | His | Glu | Leu | Gln | Glu | Lys | Leu | Ser | Pro | Leu | |
| | | | 130 | | | | | 135 | | | | | 140 | | | |
| ggc | gag | gag | atg | cgc | gac | tgc | gcg | cgc | gcc | cat | gtg | gac | gcg | ctg | cgc | 480 |

```
Gly Glu Glu Met Arg Asp Cys Ala Arg Ala His Val Asp Ala Leu Arg
145                 150                 155                 160 acg cat ctg gcc ccc tac agc gac gag ctg cgc cag cgc ttg gcc gcg    528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac    576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag    624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc    672
Pro Ala Leu Glu Asp Leu Arg Gln Gly Leu Leu Pro Val Leu Glu Ser
    210                 215                 220 ttc aag gtc agc ttc ctg agc gct ctc gag gag tac act aag aag ctc    720
Phe Lys Val Ser Phe Leu Ser Ala Leu Glu Glu Tyr Thr Lys Lys Leu
225                 230                 235                 240 aac acc cag tga                                                    732
Asn Thr Gln <210> SEQ ID NO 26
<211> LENGTH: 243
<212> TYPE: PRT
<213> ORGANISM: Homo sapiens

<400> SEQUENCE: 26

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Cys Glu Gln Leu
        50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
                100                 105                 110

Glu Leu Tyr Arg Gln Lys Val Glu Pro Leu Arg Ala Glu Leu Gln Glu
            115                 120                 125

Gly Ala Arg Gln Lys Leu His Glu Leu Gln Glu Lys Leu Ser Pro Leu
130                 135                 140

Gly Glu Glu Met Arg Asp Cys Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240
```

Asn Thr Gln

<210> SEQ ID NO 27
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R83C, R173C

<400> SEQUENCE: 27

```
gat gaa ccc ccc cag agc ccc tgg gat cga gtg aag gac ctg gcc act      48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
                20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
            35                  40                  45 aac tgg gac agc gtg acc tcc acc ttc agc aag ctg cgc gaa cag ctc     192
Asn Trp Asp Ser Val Thr Ser Thr Phe Ser Lys Leu Arg Glu Gln Leu
        50                  55                  60 ggc cct gtg acc cag gag ttc tgg gat aac ctg gaa aag gag aca gag     240
Gly Pro Val Thr Gln Glu Phe Trp Asp Asn Leu Glu Lys Glu Thr Glu
65                  70                  75                  80 ggc ctg tgc caa gag atg agc aag gat ctg gag gag gtg aag gcc aag     288
Gly Leu Cys Gln Glu Met Ser Lys Asp Leu Glu Glu Val Lys Ala Lys
                85                  90                  95 gtg cag ccc tac ctg gac gac ttc cag aag aag tgg cag gag gag atg     336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag     384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg     432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc     480
Gly Glu Glu Met Arg Asp Arg Ala Arg Ala His Val Asp Ala Leu Arg
145                 150                 155                 160 acg cat ctg gcc ccc tac agc gac gag ctg cgc cag tgc ttg gcc gcg     528
Thr His Leu Ala Pro Tyr Ser Asp Glu Leu Arg Gln Cys Leu Ala Ala
                165                 170                 175 cgc ctt gag gct ctc aag gag aac ggc ggc gcc aga ctg gcc gag tac     576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag     624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc     672
Pro Ala Leu Glu Asp Leu Arg Gln Gly Leu Leu Pro Val Leu Glu Ser
    210                 215                 220 ttc aag gtc agc ttc ctg agc gct ctc gag gag tac act aag aag ctc     720
Phe Lys Val Ser Phe Leu Ser Ala Leu Glu Glu Tyr Thr Lys Lys Leu
225                 230                 235                 240 aac acc cag tga                                                     732
Asn Thr Gln
```

<210> SEQ ID NO 28

<211> LENGTH: 243
<212> TYPE: PRT
<213> ORGANISM: Homo sapiens

<400> SEQUENCE: 28

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Cys Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 29
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R83C, R151C

<400> SEQUENCE: 29 gat gaa ccc ccc cag agc ccc tgg gat cga gtg aag gac ctg gcc act     48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag     96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac    144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc    192
Asn Trp Asp Ser Val Thr Ser Thr Phe Ser Lys Leu Arg Glu Gln Leu

```
ggc cct gtg acc cag gag ttc tgg gat aac ctg gaa aag gag aca gag    240
Gly Pro Val Thr Gln Glu Phe Trp Asp Asn Leu Glu Lys Glu Thr Glu
 65                  70                  75                  80 ggc ctg tgc caa gag atg agc aag gat ctg gag gag gtg aag gcc aag    288
Gly Leu Cys Gln Glu Met Ser Lys Asp Leu Glu Glu Val Lys Ala Lys
                 85                  90                  95 gtg cag ccc tac ctg gac gac ttc cag aag aag tgg cag gag gag atg    336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag    384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg    432
Gly Ala Arg Gln Lys Leu His Glu Leu Gln Glu Lys Leu Ser Pro Leu
130                 135                 140 ggc gag gag atg cgc gac tgc gcg cgc gcc cat gtg gac gcg ctg cgc    480
Gly Glu Glu Met Arg Asp Cys Ala Arg Ala His Val Asp Ala Leu Arg
145                 150                 155                 160 acg cat ctg gcc ccc tac agc gac gag ctg cgc cag cgc ttg gcc gcg    528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac    576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag    624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc    672
Pro Ala Leu Glu Asp Leu Arg Gln Gly Leu Leu Pro Val Leu Glu Ser
210                 215                 220 ttc aag gtc agc ttc ctg agc gct ctc gag gag tac act aag aag ctc    720
Phe Lys Val Ser Phe Leu Ser Ala Leu Glu Glu Tyr Thr Lys Lys Leu
225                 230                 235                 240 aac acc cag tga                                                    732
Asn Thr Gln
```

<210> SEQ ID NO 30
<211> LENGTH: 243
<212> TYPE: PRT
<213> ORGANISM: Homo sapiens

<400> SEQUENCE: 30

```
Asp Glu Pro Pro Gln Ser Pro Trp Asp Arg Val Lys Asp Leu Ala Thr
  1               5                  10                  15

Val Tyr Val Asp Val Leu Lys Asp Ser Gly Arg Asp Tyr Val Ser Gln
                 20                  25                  30

Phe Glu Gly Ser Ala Leu Gly Lys Gln Leu Asn Leu Lys Leu Leu Asp
             35                  40                  45

Asn Trp Asp Ser Val Thr Ser Thr Phe Ser Lys Leu Arg Glu Gln Leu
 50                  55                  60

Gly Pro Val Thr Gln Glu Phe Trp Asp Asn Leu Glu Lys Glu Thr Glu
 65                  70                  75                  80

Gly Leu Cys Gln Glu Met Ser Lys Asp Leu Glu Glu Val Lys Ala Lys
                 85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
```

```
                115                 120                 125
Gly Ala Arg Gln Lys Leu His Glu Leu Gln Glu Lys Leu Ser Pro Leu
            130                 135                 140

Gly Glu Glu Met Arg Asp Cys Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 31
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R83C, R215C

<400> SEQUENCE: 31 gat gaa ccc ccc cag agc ccc tgg gat cga gtg aag gac ctg gcc act         48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag         96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac        144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc        192
Asn Trp Asp Ser Val Thr Ser Thr Phe Ser Lys Leu Arg Glu Gln Leu
    50                  55                  60 ggc cct gtg acc cag gag ttc tgg gat aac ctg gaa aag gag aca gag        240
Gly Pro Val Thr Gln Glu Phe Trp Asp Asn Leu Glu Lys Glu Thr Glu
65                  70                  75                  80 ggc ctg tgc caa gag atg agc aag gat ctg gag gag gtg aag gcc aag        288
Gly Leu Cys Gln Glu Met Ser Lys Asp Leu Glu Glu Val Lys Ala Lys
                85                  90                  95 gtg cag ccc tac ctg gac gac ttc cag aag aag tgg cag gag gag atg        336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag        384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg        432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc        480
Gly Glu Glu Met Arg Asp Arg Ala Arg Ala His Val Asp Ala Leu Arg
145                 150                 155                 160 acg cat ctg gcc ccc tac agc gac gag ctg cgc cag cgc ttg gcc gcg        528
Thr His Leu Ala Pro Tyr Ser Asp Glu Leu Arg Gln Arg Leu Ala Ala
```

```
                   165                 170                 175
cgc ctt gag gct ctc aag gag aac ggc ggc gcc aga ctg gcc gag tac      576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag      624
His Ala Lys Ala Thr Glu His Leu Ser Thr Leu Ser Glu Lys Ala Lys
        195                 200                 205 ccc gcg ctc gag gac ctc tgc caa ggc ctg ctg ccc gtg ctg gag agc      672
Pro Ala Leu Glu Asp Leu Cys Gln Gly Leu Leu Pro Val Leu Glu Ser
    210                 215                 220 ttc aag gtc agc ttc ctg agc gct ctc gag gag tac act aag aag ctc      720
Phe Lys Val Ser Phe Leu Ser Ala Leu Glu Glu Tyr Thr Lys Lys Leu
225                 230                 235                 240 aac acc cag tga                                                      732
Asn Thr Gln <210> SEQ ID NO 32
<211> LENGTH: 243
<212> TYPE: PRT
<213> ORGANISM: Homo sapiens

<400> SEQUENCE: 32

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Cys Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Cys Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 33
<211> LENGTH: 732
```

<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R151C, R173C

<400> SEQUENCE: 33

```
gat gaa ccc ccc cag agc ccc tgg gat cga gtg aag gac ctg gcc act      48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag      96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac     144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc     192
Asn Trp Asp Ser Val Thr Ser Thr Phe Ser Lys Leu Arg Glu Gln Leu
50                  55                  60 ggc cct gtg acc cag gag ttc tgg gat aac ctg gaa aag gag aca gag     240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag     288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg     336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag     384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg     432
Gly Ala Arg Gln Lys Leu His Glu Leu Gln Glu Lys Leu Ser Pro Leu
    130                 135                 140 ggc gag gag atg cgc gac tgc gcg cgc gcc cat gtg gac gcg ctg cgc     480
Gly Glu Glu Met Arg Asp Cys Ala Arg Ala His Val Asp Ala Leu Arg
145                 150                 155                 160 acg cat ctg gcc ccc tac agc gac gag ctg cgc cag tgc ttg gcc gcg     528
Thr His Leu Ala Pro Tyr Ser Asp Glu Leu Arg Gln Cys Leu Ala Ala
                165                 170                 175 cgc ctt gag gct ctc aag gag aac ggc ggc gcc aga ctg gcc gag tac     576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag     624
His Ala Lys Ala Thr Glu His Leu Ser Thr Leu Ser Glu Lys Ala Lys
        195                 200                 205 ccc gcg ctc gag gac ctc cgc caa ggc ctg ctg ccc gtg ctg gag agc     672
Pro Ala Leu Glu Asp Leu Arg Gln Gly Leu Leu Pro Val Leu Glu Ser
    210                 215                 220 ttc aag gtc agc ttc ctg agc gct ctc gag gag tac act aag aag ctc     720
Phe Lys Val Ser Phe Leu Ser Ala Leu Glu Glu Tyr Thr Lys Lys Leu
225                 230                 235                 240 aac acc cag tga                                                     732
Asn Thr Gln
```

<210> SEQ ID NO 34
<211> LENGTH: 243
<212> TYPE: PRT
<213> ORGANISM: Homo sapiens

<400> SEQUENCE: 34

```
Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
        50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Cys Ala Arg Ala His Val Asp Ala Leu Arg
145                 150                 155                 160

Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 35
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R151C, R215C

<400> SEQUENCE: 35 gat gaa ccc ccc cag agc ccc tgg gat cga gtg aag gac ctg gcc act        48
Asp Glu Pro Pro Gln Ser Pro Trp Asp Arg Val Lys Asp Leu Ala Thr
1               5                   10                  15 gtg tac gtg gat gtg ctc aaa gac agc ggc aga gac tat gtg tcc cag        96
Val Tyr Val Asp Val Leu Lys Asp Ser Gly Arg Asp Tyr Val Ser Gln
                20                  25                  30 ttt gaa ggc tcc gcc ttg gga aaa cag cta aac cta aag ctc ctt gac       144
Phe Glu Gly Ser Ala Leu Gly Lys Gln Leu Asn Leu Lys Leu Leu Asp
            35                  40                  45 aac tgg gac agc gtg acc tcc acc ttc agc aag ctg cgc gaa cag ctc       192
Asn Trp Asp Ser Val Thr Ser Thr Phe Ser Lys Leu Arg Glu Gln Leu
        50                  55                  60 ggc cct gtg acc cag gag ttc tgg gat aac ctg gaa aag gag aca gag       240
Gly Pro Val Thr Gln Glu Phe Trp Asp Asn Leu Glu Lys Glu Thr Glu
65                  70                  75                  80
```

-continued

```
ggc ctg agg caa gag atg agc aag gat ctg gag gag gtg aag gcc aag     288
Gly Leu Arg Gln Glu Met Ser Lys Asp Leu Glu Glu Val Lys Ala Lys
                 85                  90                  95 gtg cag ccc tac ctg gac gac ttc cag aag aag tgg cag gag gag atg     336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag     384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg     432
Gly Ala Arg Gln Lys Leu His Glu Leu Gln Glu Lys Leu Ser Pro Leu
    130                 135                 140 ggc gag gag atg cgc gac tgc gcg cgc gcc cat gtg gac gcg ctg cgc     480
Gly Glu Glu Met Arg Asp Cys Ala Arg Ala His Val Asp Ala Leu Arg
145                 150                 155                 160 acg cat ctg gcc ccc tac agc gac gag ctg cgc cag cgc ttg gcc gcg     528
Thr His Leu Ala Pro Tyr Ser Asp Glu Leu Arg Gln Arg Leu Ala Ala
                165                 170                 175 cgc ctt gag gct ctc aag gag aac ggc ggc gcc aga ctg gcc gag tac     576
Arg Leu Glu Ala Leu Lys Glu Asn Gly Gly Ala Arg Leu Ala Glu Tyr
            180                 185                 190 cac gcc aag gcc acc gag cat ctg agc acg ctc agc gag aag gcc aag     624
His Ala Lys Ala Thr Glu His Leu Ser Thr Leu Ser Glu Lys Ala Lys
        195                 200                 205 ccc gcg ctc gag gac ctc tgc caa ggc ctg ctg ccc gtg ctg gag agc     672
Pro Ala Leu Glu Asp Leu Cys Gln Gly Leu Leu Pro Val Leu Glu Ser
    210                 215                 220 ttc aag gtc agc ttc ctg agc gct ctc gag gag tac act aag aag ctc     720
Phe Lys Val Ser Phe Leu Ser Ala Leu Glu Glu Tyr Thr Lys Lys Leu
225                 230                 235                 240 aac acc cag tga                                                     732
Asn Thr Gln
```

<210> SEQ ID NO 36
<211> LENGTH: 243
<212> TYPE: PRT
<213> ORGANISM: Homo sapiens

<400> SEQUENCE: 36

```
Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140
```

```
Gly Glu Glu Met Arg Asp Cys Ala Arg Ala His Val Asp Ala Leu Arg
145                 150                 155                 160

Thr His Leu Ala Pro Tyr Ser Asp Glu Leu Arg Gln Arg Leu Ala Ala
            165                 170                 175

Arg Leu Glu Ala Leu Lys Glu Asn Gly Gly Ala Arg Leu Ala Glu Tyr
        180                 185                 190

His Ala Lys Ala Thr Glu His Leu Ser Thr Leu Ser Glu Lys Ala Lys
    195                 200                 205

Pro Ala Leu Glu Asp Leu Cys Gln Gly Leu Leu Pro Val Leu Glu Ser
210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 37
<211> LENGTH: 732
<212> TYPE: DNA
<213> ORGANISM: Homo sapiens
<220> FEATURE:
<221> NAME/KEY: CDS
<222> LOCATION: (1)..(732)
<223> OTHER INFORMATION: Apo A-1 human mutein R10C, R173C

<400> SEQUENCE: 37 gat gaa ccc ccc cag agc ccc tgg gat tgt gtg aag gac ctg gcc act    48
Asp Glu Pro Pro Gln Ser Pro Trp Asp Cys Val Lys Asp Leu Ala Thr
1               5                   10                  15 gtg tac gtg gat gtg ctc aaa gac agc ggc aga gac tat gtg tcc cag    96
Val Tyr Val Asp Val Leu Lys Asp Ser Gly Arg Asp Tyr Val Ser Gln
            20                  25                  30 ttt gaa ggc tcc gcc ttg gga aaa cag cta aac cta aag ctc ctt gac   144
Phe Glu Gly Ser Ala Leu Gly Lys Gln Leu Asn Leu Lys Leu Leu Asp
        35                  40                  45 aac tgg gac agc gtg acc tcc acc ttc agc aag ctg cgc gaa cag ctc   192
Asn Trp Asp Ser Val Thr Ser Thr Phe Ser Lys Leu Arg Glu Gln Leu
    50                  55                  60 ggc cct gtg acc cag gag ttc tgg gat aac ctg gaa aag gag aca gag   240
Gly Pro Val Thr Gln Glu Phe Trp Asp Asn Leu Glu Lys Glu Thr Glu
65                  70                  75                  80 ggc ctg agg caa gag atg agc aag gat ctg gag gag gtg aag gcc aag   288
Gly Leu Arg Gln Glu Met Ser Lys Asp Leu Glu Glu Val Lys Ala Lys
                85                  90                  95 gtg cag ccc tac ctg gac gac ttc cag aag aag tgg cag gag gag atg   336
Val Gln Pro Tyr Leu Asp Asp Phe Gln Lys Lys Trp Gln Glu Glu Met
            100                 105                 110 gag ctc tac cgc cag aag gtg gag ccg ctg cgc gca gag ctc caa gag   384
Glu Leu Tyr Arg Gln Lys Val Glu Pro Leu Arg Ala Glu Leu Gln Glu
        115                 120                 125 ggc gcg cgc cag aag ctg cac gag ctg caa gag aag ctg agc cca ctg   432
Gly Ala Arg Gln Lys Leu His Glu Leu Gln Glu Lys Leu Ser Pro Leu
    130                 135                 140 ggc gag gag atg cgc gac cgc gcg cgc gcc cat gtg gac gcg ctg cgc   480
Gly Glu Glu Met Arg Asp Arg Ala Arg Ala His Val Asp Ala Leu Arg
145                 150                 155                 160 acg cat ctg gcc ccc tac agc gac gag ctg cgc cag tgc ttg gcc gcg   528
Thr His Leu Ala Pro Tyr Ser Asp Glu Leu Arg Gln Cys Leu Ala Ala
                165                 170                 175 cgc ctt gag gct ctc aag gag aac ggc ggc gcc aga ctg gcc gag tac   576
Arg Leu Glu Ala Leu Lys Glu Asn Gly Gly Ala Arg Leu Ala Glu Tyr
            180                 185                 190
```

```
cac gcc aag gcc acc gag cat ctg agc acg ctc agc gag aag gcc aag      624
His Ala Lys Ala Thr Glu His Leu Ser Thr Leu Ser Glu Lys Ala Lys
            195                 200                 205 ccc gcg ctc gag gac ctc cgc caa ggc ctg ctg ccc gtg ctg gag agc      672
Pro Ala Leu Glu Asp Leu Arg Gln Gly Leu Leu Pro Val Leu Glu Ser
    210                 215                 220 ttc aag gtc agc ttc ctg agc gct ctc gag gag tac act aag aag ctc      720
Phe Lys Val Ser Phe Leu Ser Ala Leu Glu Glu Tyr Thr Lys Lys Leu
225                 230                 235                 240 aac acc cag tga                                                       732
Asn Thr Gln <210> SEQ ID NO 38
<211> LENGTH: 243
<212> TYPE: PRT
<213> ORGANISM: Homo sapiens

<400> SEQUENCE: 38

Asp Glu Pro Pro Gln Ser Pro Trp Asp Cys Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 39
<211> LENGTH: 732
<212> TYPE: DNA
<213> ORGANISM: Homo sapiens
<220> FEATURE:
<221> NAME/KEY: CDS
<222> LOCATION: (1)..(732)
```

<223> OTHER INFORMATION: Human Apo A-1 wild type

<400> SEQUENCE: 39

| | | | | | | | | | | | | | | | | |
|---|---|---|---|---|---|---|---|---|---|---|---|---|---|---|---|---|
| gat | gaa | ccc | ccc | cag | agc | ccc | tgg | gat | cga | gtg | aag | gac | ctg | gcc | act | 48 |
| Asp | Glu | Pro | Pro | Gln | Ser | Pro | Trp | Asp | Arg | Val | Lys | Asp | Leu | Ala | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtg | tac | gtg | gat | gtg | ctc | aaa | gac | agc | ggc | aga | gac | tat | gtg | tcc | cag | 96 |
| Val | Tyr | Val | Asp | Val | Leu | Lys | Asp | Ser | Gly | Arg | Asp | Tyr | Val | Ser | Gln | |
| | | | 20 | | | | | 25 | | | | | 30 | | | |

| | | | | | | | | | | | | | | | | |
|---|---|---|---|---|---|---|---|---|---|---|---|---|---|---|---|---|
| ttt | gaa | ggc | tcc | gcc | ttg | gga | aaa | cag | cta | aac | cta | aag | ctc | ctt | gac | 144 |
| Phe | Glu | Gly | Ser | Ala | Leu | Gly | Lys | Gln | Leu | Asn | Leu | Lys | Leu | Leu | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| aac | tgg | gac | agc | gtg | acc | tcc | acc | ttc | agc | aag | ctg | cgc | gaa | cag | ctc | 192 |
| Asn | Trp | Asp | Ser | Val | Thr | Ser | Thr | Phe | Ser | Lys | Leu | Arg | Glu | Gln | Leu | |
| | 50 | | | | | 55 | | | | | 60 | | | | | |

| | | | | | | | | | | | | | | | | |
|---|---|---|---|---|---|---|---|---|---|---|---|---|---|---|---|---|
| ggc | cct | gtg | acc | cag | gag | ttc | tgg | gat | aac | ctg | gaa | aag | gag | aca | gag | 240 |
| Gly | Pro | Val | Thr | Gln | Glu | Phe | Trp | Asp | Asn | Leu | Glu | Lys | Glu | Thr | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggc | ctg | agg | caa | gag | atg | agc | aag | gat | ctg | gag | gag | gtg | aag | gcc | aag | 288 |
| Gly | Leu | Arg | Gln | Glu | Met | Ser | Lys | Asp | Leu | Glu | Glu | Val | Lys | Ala | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| gtg | cag | ccc | tac | ctg | gac | gac | ttc | cag | aag | aag | tgg | cag | gag | gag | atg | 336 |
| Val | Gln | Pro | Tyr | Leu | Asp | Asp | Phe | Gln | Lys | Lys | Trp | Gln | Glu | Glu | Met | |
| | | | 100 | | | | | 105 | | | | | 110 | | | |

| | | | | | | | | | | | | | | | | |
|---|---|---|---|---|---|---|---|---|---|---|---|---|---|---|---|---|
| gag | ctc | tac | cgc | cag | aag | gtg | gag | ccg | ctg | cgc | gca | gag | ctc | caa | gag | 384 |
| Glu | Leu | Tyr | Arg | Gln | Lys | Val | Glu | Pro | Leu | Arg | Ala | Glu | Leu | Gln | Glu | |
| | | | 115 | | | | | 120 | | | | | 125 | | | |

| | | | | | | | | | | | | | | | | |
|---|---|---|---|---|---|---|---|---|---|---|---|---|---|---|---|---|
| ggc | gcg | cgc | cag | aag | ctg | cac | gag | ctg | caa | gag | aag | ctg | agc | cca | ctg | 432 |
| Gly | Ala | Arg | Gln | Lys | Leu | His | Glu | Leu | Gln | Glu | Lys | Leu | Ser | Pro | Leu | |
| | | 130 | | | | | 135 | | | | | 140 | | | | |

| | | | | | | | | | | | | | | | | |
|---|---|---|---|---|---|---|---|---|---|---|---|---|---|---|---|---|
| ggc | gag | gag | atg | cgc | gac | cgc | gcg | cgc | gcc | cat | gtg | gac | gcg | ctg | cgc | 480 |
| Gly | Glu | Glu | Met | Arg | Asp | Arg | Ala | Arg | Ala | His | Val | Asp | Ala | Leu | Arg | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| acg | cat | ctg | gcc | ccc | tac | agc | gac | gag | ctg | cgc | cag | cgc | ttg | gcc | gcg | 528 |
| Thr | His | Leu | Ala | Pro | Tyr | Ser | Asp | Glu | Leu | Arg | Gln | Arg | Leu | Ala | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| cgc | ctt | gag | gct | ctc | aag | gag | aac | ggc | ggc | gcc | aga | ctg | gcc | gag | tac | 576 |
| Arg | Leu | Glu | Ala | Leu | Lys | Glu | Asn | Gly | Gly | Ala | Arg | Leu | Ala | Glu | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| cac | gcc | aag | gcc | acc | gag | cat | ctg | agc | acg | ctc | agc | gag | aag | gcc | aag | 624 |
| His | Ala | Lys | Ala | Thr | Glu | His | Leu | Ser | Thr | Leu | Ser | Glu | Lys | Ala | Lys | |
| | | 195 | | | | | 200 | | | | | 205 | | | | |

| | | | | | | | | | | | | | | | | |
|---|---|---|---|---|---|---|---|---|---|---|---|---|---|---|---|---|
| ccc | gcg | ctc | gag | gac | ctc | cgc | caa | ggc | ctg | ctg | ccc | gtg | ctg | gag | agc | 672 |
| Pro | Ala | Leu | Glu | Asp | Leu | Arg | Gln | Gly | Leu | Leu | Pro | Val | Leu | Glu | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| ttc | aag | gtc | agc | ttc | ctg | agc | gct | ctc | gag | gag | tac | act | aag | aag | ctc | 720 |
| Phe | Lys | Val | Ser | Phe | Leu | Ser | Ala | Leu | Glu | Glu | Tyr | Thr | Lys | Lys | Leu | |
| 225 | | | | | 230 | | | | | 235 | | | | | 240 | |

| | | | |
|---|---|---|---|
| aac | acc | cag | tga | 732 |
| Asn | Thr | Gln | | |

<210> SEQ ID NO 40
<211> LENGTH: 243
<212> TYPE: PRT
<213> ORGANISM: Homo sapiens

<400> SEQUENCE: 40

| | | | | | | | | | | | | | | | |
|---|---|---|---|---|---|---|---|---|---|---|---|---|---|---|---|
| Asp | Glu | Pro | Pro | Gln | Ser | Pro | Trp | Asp | Arg | Val | Lys | Asp | Leu | Ala | Thr |
| 1 | | | | 5 | | | | | 10 | | | | | 15 | |

| | | | | | | | | | | | |
|---|---|---|---|---|---|---|---|---|---|---|---|
| Val | Tyr | Val | Asp | Val | Leu | Lys | Asp | Ser | Gly | Arg | Asp | Tyr | Val | Ser | Gln |

-continued

```
                    20                  25                  30
Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
        130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
            165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln
```